(12) United States Patent
Moffitt et al.

(10) Patent No.: US 11,344,732 B2
(45) Date of Patent: May 31, 2022

(54) MULTIPLE MODE NEUROMODULATION RESPONSIVE TO PATIENT INFORMATION

(71) Applicant: Boston Scientific Neuromodulation Corporation, Valencia, CA (US)

(72) Inventors: Michael A. Moffitt, Solon, OH (US); Sridhar Kothandaraman, Valencia, CA (US); Chirag Shah, Valencia, CA (US); Vikrant Venkateshwar Gunna Srinivasan, Los Angeles, CA (US); Richard Mustakos, Simi Valley, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 194 days.

(21) Appl. No.: 16/396,377

(22) Filed: Apr. 26, 2019

(65) Prior Publication Data

US 2019/0329051 A1 Oct. 31, 2019

Related U.S. Application Data

(60) Provisional application No. 62/663,565, filed on Apr. 27, 2018.

(51) Int. Cl.
*A61N 1/372* (2006.01)
*A61N 1/36* (2006.01)
*A61N 1/05* (2006.01)

(52) U.S. Cl.
CPC ........ *A61N 1/37264* (2013.01); *A61N 1/0534* (2013.01); *A61N 1/3614* (2017.08);
(Continued)

(58) Field of Classification Search
CPC .............. A61N 1/0534; A61N 1/36062; A61N 1/36067; A61N 1/36132; A61N 1/36135;
(Continued)

(56) References Cited

U.S. PATENT DOCUMENTS

| 6,560,490 B2 | 5/2003 | Grill et al. |
| 7,742,810 B2 | 6/2010 | Moffitt et al. |

(Continued)

FOREIGN PATENT DOCUMENTS

| WO | WO-2013086215 A1 | 6/2013 |
| WO | WO-2019210117 A1 | 10/2019 |

OTHER PUBLICATIONS

McIntyre, Cameron C, et al., "Excitation of central nervous system neurons by nonuniform electric fields.", Biophys. J., 76(2), (1999), 878-888.

(Continued)

*Primary Examiner* — Christopher A Flory
(74) *Attorney, Agent, or Firm* — Schwegman Lundberg & Woessner, P.A.

(57) ABSTRACT

A system may comprise a controller configured to implement an algorithm on a received input to produce an output, and a system input operably connected to the controller and configured for use to enter at least one input into the algorithm. The at least one input may include: one or more sensor inputs or one or more inputs from smart appliances or one or more user inputs regarding at least one of time of day or mental or physical state; or at least one of a user-inputted disease, a user-inputted disease state, or a user-inputted symptom-related information into the algorithm. The controller may be configured to provide instructions through the system output to implement a system action. The algorithm implemented by the controller may be configured to identify one, or a combination of more than one, of the neuromodulation modes as a candidate neuromodulation mode based on the input(s).

20 Claims, 12 Drawing Sheets

(52) U.S. Cl.
CPC ..... *A61N 1/36062* (2017.08); *A61N 1/36067* (2013.01); *A61N 1/36132* (2013.01); *A61N 1/36135* (2013.01); *A61N 1/37247* (2013.01)

(58) Field of Classification Search
CPC .............. A61N 1/3614; A61N 1/37257; A61N 1/37264
See application file for complete search history.

(56) References Cited

U.S. PATENT DOCUMENTS

| | | | |
|---|---|---|---|
| 7,979,119 B2 | 7/2011 | Kothandaraman et al. | |
| 7,987,000 B2 | 7/2011 | Moffitt et al. | |
| 8,055,337 B2 | 11/2011 | Moffitt et al. | |
| 8,190,250 B2 | 5/2012 | Moffitt | |
| 8,412,345 B2 | 4/2013 | Moffitt | |
| 8,543,200 B2 | 9/2013 | Lane et al. | |
| 8,660,644 B2 | 2/2014 | Jaax et al. | |
| 8,676,308 B2 | 3/2014 | Moffitt et al. | |
| 8,849,411 B2 | 9/2014 | Moffitt et al. | |
| 9,008,783 B2 | 4/2015 | Moffitt et al. | |
| 9,259,588 B2 | 2/2016 | Rao et al. | |
| 9,314,639 B2 | 4/2016 | Rao et al. | |
| 9,327,107 B2 | 5/2016 | Moffitt | |
| 9,440,079 B2 | 9/2016 | Moffitt et al. | |
| 9,504,818 B2 | 11/2016 | Moffitt et al. | |
| 9,586,053 B2 | 3/2017 | Moffitt et al. | |
| 9,604,058 B2 | 3/2017 | Moffitt | |
| 9,623,244 B2 | 4/2017 | Kothandaraman | |
| 9,656,085 B2 | 5/2017 | Moffitt et al. | |
| 9,737,715 B2 | 8/2017 | Moffitt et al. | |
| 9,750,939 B2 | 9/2017 | Carcieri et al. | |
| 9,764,141 B2 | 9/2017 | Moffitt et al. | |
| 9,814,880 B2 | 11/2017 | Hershey et al. | |
| 9,849,287 B2 | 12/2017 | Hershey et al. | |
| 9,855,432 B2 | 1/2018 | Yoo et al. | |
| 9,878,166 B2 | 1/2018 | Thacker et al. | |
| 9,884,196 B2 | 2/2018 | Rao et al. | |
| 9,925,380 B2 | 3/2018 | Moffitt et al. | |
| 9,974,960 B2 | 5/2018 | Steinke et al. | |
| 10,010,715 B2 | 7/2018 | Zhu et al. | |
| 10,029,102 B2 | 7/2018 | Doan et al. | |
| 10,086,207 B2 | 10/2018 | Wechter et al. | |
| 2007/0156207 A1 | 7/2007 | Kothandaraman et al. | |
| 2007/0162086 A1* | 7/2007 | DiLorenzo ........... A61B 5/4082 | 607/45 |
| 2007/0167991 A1* | 7/2007 | DiLorenzo ........... A61B 5/0816 | 607/45 |
| 2009/0082640 A1* | 3/2009 | Kovach ................ A61B 5/7435 | 600/300 |
| 2009/0082641 A1* | 3/2009 | Giftakis ................ G16H 40/63 | 600/300 |
| 2009/0082829 A1* | 3/2009 | Panken ................ A61M 5/1723 | 607/45 |
| 2009/0083070 A1* | 3/2009 | Giftakis ............. A61N 1/37247 | 705/2 |
| 2010/0057164 A1 | 3/2010 | Moffitt et al. | |
| 2010/0121409 A1 | 5/2010 | Kothandaraman et al. | |
| 2010/0268298 A1 | 10/2010 | Moffitt et al. | |
| 2010/0280500 A1* | 11/2010 | Skelton ............. A61M 5/14276 | 604/891.1 |
| 2011/0029044 A1* | 2/2011 | Hyde ................. A61N 1/36139 | 607/62 |
| 2011/0040546 A1* | 2/2011 | Gerber ..................... A61N 1/37 | 703/11 |
| 2011/0208012 A1* | 8/2011 | Gerber ............... A61N 1/37235 | 600/300 |
| 2011/0282414 A1 | 11/2011 | Kothandaraman et al. | |
| 2012/0109230 A1 | 5/2012 | Kothandaraman et al. | |
| 2012/0165898 A1* | 6/2012 | Moffitt ............... A61N 1/36067 | 607/45 |
| 2012/0303087 A1* | 11/2012 | Moffitt ............... A61N 1/37241 | 607/45 |
| 2013/0060305 A1* | 3/2013 | Bokil ................. A61N 1/36146 | 607/62 |
| 2013/0131755 A1* | 5/2013 | Panken ................... G06F 3/015 | 607/45 |
| 2014/0067022 A1* | 3/2014 | Carcieri ............... A61N 1/0534 | 607/62 |
| 2014/0074179 A1* | 3/2014 | Heldman ........... A61N 1/36135 | 607/45 |
| 2014/0074180 A1* | 3/2014 | Heldman ............. A61N 1/0534 | 607/45 |
| 2014/0277267 A1 | 9/2014 | Vansickle et al. | |
| 2015/0005842 A1 | 1/2015 | Lee et al. | |
| 2015/0073504 A1 | 3/2015 | Kothandaraman et al. | |
| 2015/0165209 A1 | 6/2015 | Grandhe et al. | |
| 2016/0045751 A1 | 2/2016 | Jiang et al. | |
| 2016/0067495 A1* | 3/2016 | Chaturvedi ........ A61N 1/36132 | 607/59 |
| 2016/0144186 A1* | 5/2016 | Kaemmerer ....... A61N 1/36096 | 607/45 |
| 2016/0158553 A1* | 6/2016 | Panken ................. A61N 1/3605 | 607/45 |
| 2016/0375248 A1 | 12/2016 | Carcieri et al. | |
| 2017/0050035 A1* | 2/2017 | Gupta ................ A61N 1/36021 | |
| 2017/0056642 A1 | 3/2017 | Moffitt et al. | |
| 2017/0056663 A1* | 3/2017 | Kaemmerer ....... A61N 1/37247 | |
| 2017/0072207 A1 | 3/2017 | Howard et al. | |
| 2017/0157404 A1 | 6/2017 | Moffitt et al. | |
| 2017/0326365 A1 | 11/2017 | Lane et al. | |
| 2017/0361093 A1* | 12/2017 | Yoo ...................... A61N 1/0553 | |
| 2017/0372039 A1 | 12/2017 | Mustakos et al. | |
| 2018/0056078 A1 | 3/2018 | Kashyap et al. | |
| 2018/0085583 A1 | 3/2018 | Zhang et al. | |
| 2018/0104500 A1 | 4/2018 | Blum et al. | |
| 2018/0133507 A1* | 5/2018 | Malchano .......... A61N 1/36036 | |
| 2018/0272142 A1 | 9/2018 | Zhang et al. | |
| 2018/0361153 A1* | 12/2018 | Heldman ........... A61N 1/36139 | |
| 2019/0046800 A1 | 2/2019 | Doan et al. | |

OTHER PUBLICATIONS

McIntyre, Cameron C, et al., "Selective Microstimulation of Central Nervous System Neurons", Annals of Biomedical Engineering., 28(3), (Mar. 2000), 219-233.

Mustakos, Richard, et al., "Systems and Methods for Clinical Effect-Based Neurostimulation,", U.S. Appl. No. 16/219,551, filed Dec. 13, 2018.

"International Application Serial No. PCT/US2019/029263, International Preliminary Report on Patentability dated Nov. 5, 2020", 7 pgs.

"International Application Serial No. PCT/US2019/029263, International Search Report dated Aug. 19, 2019", 3 pgs.

"International Application Serial No. PCT/US2019/029263, Written Opinion dated Aug. 19, 2019", 5 pgs.

* cited by examiner

US 11,344,732 B2

MULTIPLE MODE NEUROMODULATION RESPONSIVE TO PATIENT INFORMATION

CLAIM OF PRIORITY

This application claims the benefit of priority under 35 U.S.C. § 119(e) of U.S. Provisional Patent Application Ser. No. 62/663,565, filed on Apr. 27, 2018, which is herein incorporated by reference in its entirety.

TECHNICAL FIELD

The present disclosure relates generally to medical devices, and more particularly, to neuromodulation systems, devices, and methods.

BACKGROUND

Neuromodulation, also referred to as neurostimulation, has been proposed as a therapy for a number of conditions. Examples of neuromodulation include Spinal Cord Stimulation (SCS), Deep Brain Stimulation (DBS), Peripheral Nerve Stimulation (PNS), and Functional Electrical Stimulation (FES). Implantable neuromodulation systems have been applied to deliver such a therapy. An implantable neuromodulation system may include an implantable neuromodulation, which may also be referred to as an implantable pulse generator (IPG), and one or more implantable leads each including one or more electrodes. The implantable neuromodulation delivers neuromodulation energy through one or more electrodes placed on or near a target site in the nervous system. An external programming device is used to program the implantable neurotnodulation with parameters controlling the delivery of the neuromodulation energy. For example, the neuromodulation energy may be delivered in the form of electrical pulses using parameters that specify spatial (where to stimulate), temporal (when to stimulate), and informational (patterns of pulses directing the nervous system to respond as desired) aspects of a pattern of pulses.

The human nervous systems use neural signals having sophisticated patterns. Also, as the condition of the patient may change while receiving a neuromodulation therapy, the neuromodulation applied to the patient may need to be changed to maintain efficacy while minimizing the unintended and undesirable effects. Therefore, there is a need to provide neuromodulation systems capable of such complex neuromodulation and a need to provide efficient and accurate programming of such systems.

SUMMARY

This Summary includes examples that provide an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

An example (e.g. Example 1) of a system is for use with multiple neuromodulation modes for delivering neuromodulation therapy. The system may comprise a controller configured to implement an algorithm on a received input to produce an output, and a system input operably connected to the controller and configured for use to enter at least one input into the algorithm. The at least one input may include: one or more sensor inputs or one or more inputs from smart appliances or one or more user inputs regarding at least one of time of day or mental or physical state; or at least one of a user-inputted disease, a user-inputted disease state, or a user-inputted symptom-related information into the algorithm. The system may include a system output operably connected to controller, wherein the controller is configured to provide instructions through the system output to implement a system action. The algorithm implemented by the controller may be configured to identify one, or a combination of more than one, of the neuromodulation modes as a candidate neuromodulation mode based on the at least one input, and provide instructions through the system output for the system to implement the system action based on the candidate neuromodulation mode. The system action may include at least one of: implementing, or delivering a recommendation for implementing, the candidate neuromodulation mode; implementing, or delivering a recommendation for implementing, clinician programmer settings for use in programming a neuromodulator to deliver the neuromodulation therapy; delivering a recommendation regarding choice of an implantable pulse generator, choice of parameter value, or choice of surgical target based on the candidate neuromodulation mode; or delivering information regarding the candidate neuromodulation mode to at least one other algorithm that supports the multiple neuromodulation modes.

In Example 2, the subject matter of Example 1 may optionally be configured such that the multiple neuromodulation modes include an anodic neuromodulation mode and a cathodic neuromodulation mode.

In Example 3, the subject matter of Example 2 may optionally be configured such that the multiple neuromodulation modes include a mixed neuromodulation mode that includes anodic and cathodic neuromodulation.

In Example 4, the subject matter of Example 3 may optionally be configured such that the mixed neuromodulation mode provides a temporal mix with anodic neuromodulation during a time and cathodic neuromodulation during another time.

In Example 5, the subject matter of any one or any combination of Examples 3-4 may optionally be configured such that the mixed neuromodulation mode provides a spatial mix with a field shape to provide anodic neuromodulation in a first region of the field shape and cathodic neuromodulation in a second region of the field shape.

In Example 6, the subject matter of any one or any combination of Examples 1-5 may optionally be configured such that the multiple neuromodulation modes include neuromodulation modes for delivering different pulse shapes, or different modulation field shapes.

In Example 7, the subject matter of any one or any combination of Examples 1-6 may optionally be configured such that the system input is configured for use to enter the user-inputted disease and at least one user-inputted symptom-related information for the user-inputted disease.

In Example 8, the subject matter of Example 7 may optionally be configured such that the user-inputted disease includes Parkinson's disease.

In Example 9, the subject matter of Example 8 may optionally be configured such that the at least one user-inputted symptom-related information includes a score for at least one of bradykinesia, rigidity, or tremor, and the algorithm implemented by the controller is configured to identify one of the neuromodulation modes as the candidate neuromodulation mode based on the score for the at least one of bradykinesia, rigidity, or tremor.

In Example 10, the subject matter of Example 7 may optionally be configured such that the user-inputted disease includes a neurodegenerative disease, wherein the user-inputted symptom-related information includes a stage of the neurodegenerative disease.

In Example 11, the subject matter of Example 1 may optionally be configured such that the user-inputted symptom-related information includes a stage of Parkinson's disease, including at least one of mild, moderate, severe, at least a portion of Unified Parkinson's Disease Rating Scale, Hoehn & Yahr, and medication resistant.

In Example 12, the subject matter of any one or any combination of Examples 1-11 may optionally be configured such that the system input is configured for use to enter user-inputted side effects.

In Example 13, the subject matter of any one or any combination of Examples 1-12 may optionally be configured such that the neuromodulation therapy includes deep brain stimulation (DBS).

In Example 14, the subject matter of any one or any combination of Examples 1-12 may optionally be configured such that the neuromodulation therapy includes spinal cord stimulation (SCS).

In Example 15, the subject matter of any one or any combination of Examples 1-14 may optionally be configured such that the at least one input includes the at least one sensor input. The system may further comprise at least one sensor to provide the at least one sensor input to the algorithm. The at least one sensor may include at least one of: a sensor of impedance; a sensor of brain activity; activity in the spinal cord, dorsal horn or dorsal root; or a sensor of physical activity or physical state.

An example (e.g. Example 16) of a method implemented by a system configured for use with multiple neuromodulation modes for delivering neuromodulation therapy may include: entering at least one input into an algorithm. The at least one input may include at least one of: one or more sensor inputs or one or more inputs from smart appliances or one or more user inputs regarding at least one of time of day or mental or physical state; or at least one of a user-inputted disease, a user-inputted disease state, a user-inputted symptom-related information, or a user-inputted side effect. The method may include implementing the algorithm to identify one, or a combination of more than one, of the neuromodulation modes as a candidate neuromodulation mode based on the at least one user input, and output instructions for implementing a system action based on the candidate neuromodulation mode. The system action for the candidate neuromodulation mode may include at least one of: implementing, or delivering a recommendation for implementing, the candidate neuromodulation mode; implementing, or delivering a recommendation for implementing, clinician programmer settings for use in programming a neuromodulator to deliver the neuromodulation therapy; delivering a recommendation regarding choice of IPG, choice of parameter value, or choice of surgical target based on the candidate neuromodulation mode; or delivering information regarding the candidate neuromodulation mode to at least one other algorithm that supports the multiple neuromodulation modes.

In Example 17, the subject matter of Example 16 may optionally be configured such that the multiple neuromodulation modes include an anodic neuromodulation mode and a cathodic neuromodulation mode.

In Example 18, the subject matter of Example 17 may optionally be configured such that the multiple neuromodulation modes include a mixed neuromodulation mode that includes anodic and cathodic neuromodulation.

In Example 19, the subject matter of Example 18 may optionally be configured such that the mixed neuromodulation mode provides a temporal mix with anodic neuromodulation during a time and cathodic neuromodulation during another time.

In Example 20, the subject matter of Example 18 may optionally be configured such that the mixed neuromodulation mode provides a spatial mix with a field shape to provide anodic neuromodulation in a first region of the field shape and cathodic neuromodulation in a second region of the field shape.

In Example 21, the subject matter of Example 16 may optionally be configured such that the multiple neuromodulation modes include a neuromodulation mode for delivering neuromodulation that preferentially modulates tissue inclusive of cell bodies and another neuromodulation mode for delivering neuromodulation that preferentially modulates neuron fibers.

In Example 22, the subject matter of Example 16 may optionally be configured such that the multiple neuromodulation modes include neuromodulation modes for delivering different pulse shapes, or different modulation field shapes.

In Example 23, the subject matter of Example 16 may optionally be configured such that implementing the algorithm includes implementing the algorithm using an external programming system or a neuromodulator. The external programming system may be configured to program the neuromodulator configured to deliver the neuromodulation therapy.

In Example 24, the subject matter of Example 16 may optionally be configured such that entering the input includes entering at least one user-inputted symptom-related information.

In Example 25, the subject matter of Example 24 may optionally be configured such that the at least one user-inputted symptom-related information relates to Parkinson's disease.

In Example 26, the subject matter of Example 25 may optionally be configured such that the at least one user-inputted symptom-related information includes a score for at least one of bradykinesia, rigidity, or tremor, and implementing the algorithm to identify one of the neuromodulation modes as the candidate neuromodulation mode is based on the score for the at least one of bradykinesia, rigidity, or tremor.

In Example 27, the subject matter of Example 25 may optionally be configured such that the at least one user-inputted symptom-related information includes a score for at least one of freezing of gait, gait, axial symptoms, dementia, and dyskinesias, and implementing the algorithm to identify one of the neuromodulation modes as the candidate neuromodulation mode is based on the score for the at least one of freezing of gait, gait, axial symptoms, dementia, and dyskinesias.

In Example 28, the subject matter of Example 16 may optionally be configured such that the at least one user-inputted symptom-related information further includes medication usage or energy usage for the neuromodulation therapy.

In Example 29, the subject matter of Example 16 may optionally be configured such that the user-inputted disease includes a neurodegenerative disease, wherein entering the input further includes entering a stage of the neurodegenerative disease.

In Example 30, the subject matter of Example 16 may optionally be configured such that entering the input includes entering a stage of Parkinson's disease, including at least one of mild, moderate, severe, at least a portion of Unified Parkinson's Disease Rating Scale, Hoehn & Yahr, and medication resistant.

In Example 31, the subject matter of Example 16 may optionally be configured such that entering the input includes entering user-inputted side effects.

In Example 32, the subject matter of Example 16 may optionally be configured such that the neuromodulation therapy includes deep brain stimulation (DBS).

In Example 33, the subject matter of Example 16 may optionally be configured such that the neuromodulation therapy includes spinal cord stimulation (SCS).

In Example 34, the subject matter of Example 16 may optionally be configured such that the at least one input includes the at least one sensor input and the system further includes at least one sensor to provide the at least one sensor input to the algorithm. The at least one sensor may include at least one of: a sensor of impedance; a sensor of brain activity; a sensor of activity in the spinal cord, dorsal horn or dorsal root; or a sensor of physical activity or physical state.

An example (e.g. Example 35) of a non-transitory machine-readable medium including instructions, which when executed by a machine, cause the machine to enter at least one input into an algorithm. The at least one input includes at least one of: one or more sensor inputs or one or more user inputs regarding at least one of time of day or mental or physical state; or at least one of a user-inputted disease, a user-inputted disease state, a user-inputted symptom-related information, or a user-inputted side effect. The instructions, which when executed by the machine, may cause the machine to implement the algorithm to identify one of the neuromodulation modes as a candidate neuromodulation mode based on the at least one user input, and output instructions for implementing an action for the candidate neuromodulation mode. The action for the candidate neuromodulation mode may include at least one of: implementing, or delivering a recommendation for implementing, the candidate neuromodulation mode; implementing, or delivering a recommendation for implementing, clinician programmer settings for use in programming a neuromodulator to deliver the neuromodulation therapy; delivering a recommendation regarding choice of IPG, choice of parameter value, or choice of surgical target based on the candidate neuromodulation mode; or delivering information regarding the candidate neuromodulation mode to at least one other algorithm that supports the multiple neuromodulation modes.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Figure 1:
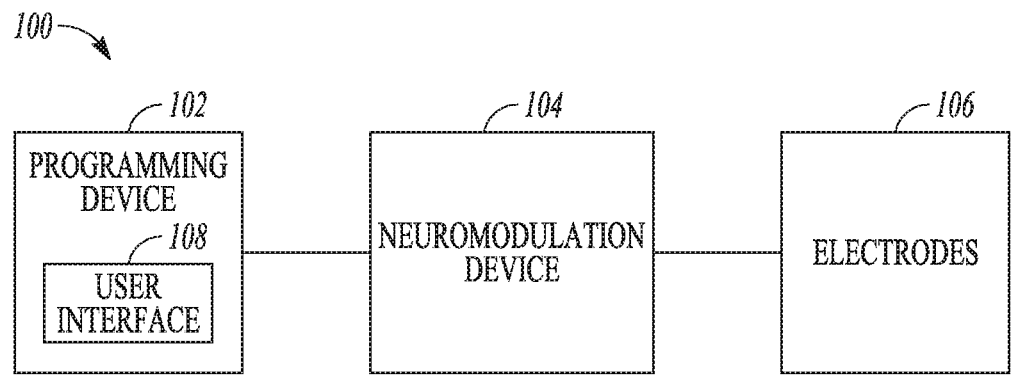
FIG. 1 illustrates, by way of example and not limitation, an embodiment of a neuromodulation system.

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

As identified above, the human nervous systems use neural signals having sophisticated patterns. Various diseases and/or disease states may respond to different types of neuromodulation. Various embodiments of the present subject matter use information about the patient being treated to determine which stimulation mode (e.g., anodic monopolar or cathodic monopolar; preferential to cells or preferential to fibers; and the like) is expected to provide the optimal therapy. The system is capable of multiple stimulation modes, and may use patient information as input(s) to algorithm to estimate which stimulation mode or modes would best serve the patient. The system may perform an action based on the estimate, such as provide information or recommendation(s) to a patient or clinician, configure a programmer with patient-specific settings, and set inputs for "next-layer" algorithms so that they best serve the patient and clinician. By way of example, the system may estimate, based on the input(s), that anodic neuromodulation is the therapy and that the best place to deliver the anodic neuromodulation therapy is at a particular location. The system may use this information to output location information to the neurosurgeon, and provide a map for where to place the lead to treat the disease that is most amenable to anodic neuromodulation.

For example, different types of neural structures have different reactions to different neuromodulation polarities. For example, cathodic neuromodulation may have a tendency to preferentially modulate neuron fibers, and anodic neuromodulation may have a tendency to preferentially modulate tissue inclusive of cell bodies. Although conventional DBS has used cathodic neuromodulation, it is believed that anodic neuromodulation for DBS may benefit some patients more than cathodic stimulation. Thus, it is believed that a particular disease may respond better to anodic stimulation, and another disease may respond better to cathodic stimulation, and yet another disease may response better to a mixed or balanced or nearly balanced neuromodulation (at least some percentage of anodic neuromodulation and at least some percentage of cathodic neuromodulation). Further, cathodic neuromodulation of one region may improve one or more symptoms of a disease and anodic neuromodulation of the same or different region may improve one or more other symptoms of the disease. Additional properties of the neuromodulation therapy may also contribute to the preferential modulation of some tissue over other tissue. Examples of such properties may include proximity of the tissue to an electrode, the size of the neural element, the trajectory/geometry of the neural element, the proximity of the cell body (or dendrites, or axon), the biophysical properties such as ion channels and distribution in the neural element, the synaptic machinery of the neural element, and the like.

In various examples, the neuromodulation system may include an implantable device configured to deliver neuromodulation therapies, such as DBS, SCS and PNS including vagus nerve stimulation (VNS), and one or more external devices configured to program the implantable device for its operations and monitor the performance of the implantable device. While DBS is discussed as a specific example, the present subject matter may also be applied to program stimulation devices for delivering various types of neuromodulation therapies.

The neuromodulation system may determine one or more stimulation parameters to modulate a target, such as a stimulation current and an electrical current fractionalization across a plurality of electrodes. The current fractionalization refers to current distribution among electrodes, and may be represented by percentage cathodic current, percentage anodic current, or off (no current allocation). Although current fractionalization is discussed in this document, it is to be understood that voltage or electrical energy may similarly be fractionalized among the electrodes, which may result in a particular spatial distribution of the stimulation field.

FIG. 1 illustrates, by way of example and not limitation, an embodiment of a neuromodulation system 100. The system 100 may, for example, be configured for DBS applications. Such DBS configuration includes various features that may simplify the task of the user in programming the stimulation device 104 for delivering DBS to the patient, such as the features discussed in this document. The illustrated system 100 includes a programming device 102, a neuromodulation device 104, and electrodes 106. The electrodes 106 may be configured for placement on or near one or more neural targets in a patient. The stimulation device 104 may be configured to be electrically connected to the electrodes 106 and deliver neuromodulation energy, such as in the form of electrical pulses, to the one or more neural targets though the electrodes 106. In an example, the neuromodulation device 104 controls the delivery of neuromodulation energy according to a plurality of neuromodulation parameters, such as a selection of active electrodes for passing neuromodulation energy to the tissue, or stimulation pattern of the electrical pulses, among others. In various examples, at least some of the neuromodulation parameters are programmable by a user, such as a clinician.

The programming device 102 may be configured to be in communication with the neuromodulation device 104 via a wired or wireless link. The programming device 102 may provide the user with accessibility to user-programmable parameters. In the illustrated example, the programming device 102 may include a user interface 108 that allows a user to control the operation of the system 100 and monitor the performance of the system 100 as well as conditions of the patient including responses to the delivery of the neuromodulation. The user may control the operation of the system 100 by setting and/or adjusting values of the user-programmable parameters. In various examples, the user interface 108 may include a graphical user interface (GUI) that allows the user to create and/or edit graphical representations of various neuromodulation waveforms. The GUI may also allow the user to set and/or adjust neuromodulation fields each defined by a set of electrodes through which one or more electrical pulses represented by a waveform are delivered to the patient. The neuromodulation fields may each be further defined by the current fractionalization across the set of electrodes. In various examples, electrical pulses for a stimulation period (such as the duration of a therapy session) may be delivered to multiple neuromodulation fields.

In this document, a "user" includes a physician or other clinician or caregiver who treats the patient using the system 100; a "patient" includes a person who receives, or is intended to receive, neurostimulation via the system 100. In various examples, the patient may be allowed to adjust his or her treatment using system 100 to certain extent, such as by adjusting certain therapy parameters and entering feedback and clinical effect information.

Figure 2:
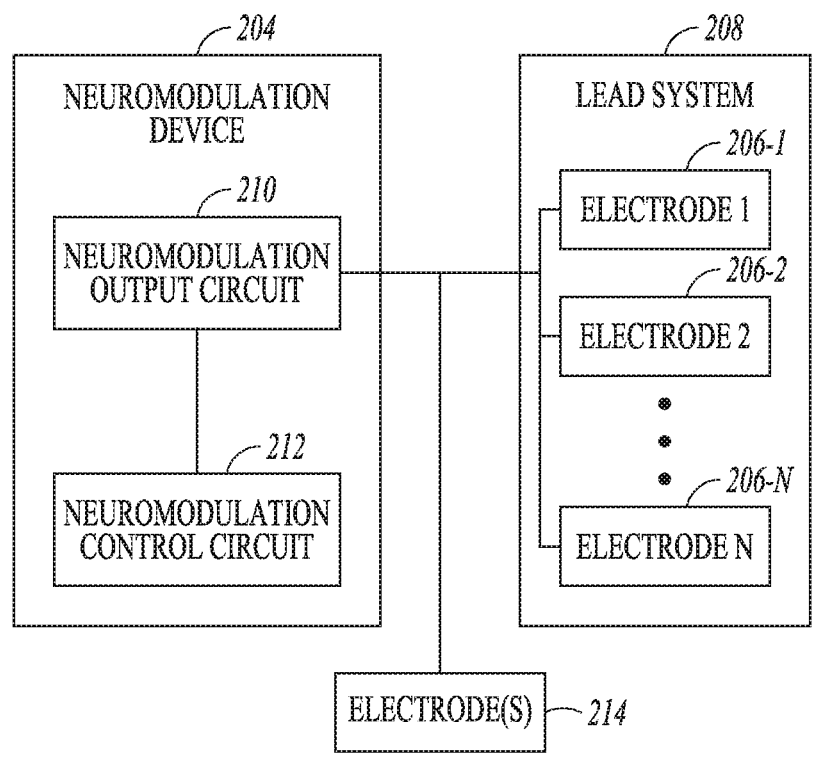
FIG. 2 illustrates, by way of example and not limitation, an embodiment of a stimulation device and a lead system, such as may be implemented in the neuromodulation system.

FIG. 2 illustrates, by way of example and not limitation, an embodiment of a stimulation device 204 and a lead system 208, such as may be implemented in the neuromodulation system 100. The neuromodulation device 204 represents an embodiment of neuromodulation device 104, and includes a neuromodulation output circuit 210 and a neuromodulation control circuit 212. The neuromodulation output circuit 210 may produce and deliver electrical pulses. The neuromodulation control circuit 212 may control the delivery of the electrical pulses from the neuromodulation output circuit 210 according to a plurality of parameters. The lead system 214 includes one or more leads each configured to be electrically connected to neuromodulation device 204 and a plurality of electrodes (including electrode 206-1, 206-2, . . . , 206-N) distributed in the one or more leads. Each of the electrodes has an electrically conductive contact providing for an electrical interface between the neuromodulation output circuit 210 and patient tissue. The number of leads within the lead system, the number of electrodes on the leads, the leady types, and the type of electrodes (e.g. ring, segmented) may vary among the various embodiments.

The electrical pulses may be delivered from the neuromodulation output circuit 212 through a set of electrodes selected from the electrodes 206. In various examples, the electrical pulses may include one or more individually defined pulses, and the set of electrodes may be individually definable by the user for each of the individually defined pulses or each of collections of pulses intended to be delivered using the same combination of electrodes. In various examples, one or more additional electrodes 214 (referred to as reference electrodes) may be electrically connected to the neuromodulation device 204, such as one or more electrodes each being a portion of or otherwise incorporated onto a housing of the neuromodulation device 204. Electrodes on the housing may be referred to as "can electrodes". The neuromodulation may be delivered as a unipolar, bipolar, or multipolar stimulation. Monopolar stimulation uses a monopolar electrode configuration with one or more electrodes selected from the electrodes within the lead system 208 and at least one electrode from electrode(s) 214. Bipolar stimulation uses a bipolar electrode configuration with two electrodes selected front the electrodes within the lead system 208 and none of the electrode(s) 214. The bipolar stimulation may include balanced or unbalanced bipolar mode using a pair of electrodes on a lead, with the balancing current being applied to a reference electrode. Some bipolar stimulation may approximate a monopolar field, and thus may be considered to be a substantially monopolar field or a pseudo-monopolar field. By way of example and not limitation, a first electrode E1 may contribute 100% of the positive current, a second electrode E2 may contribute a small percentage of the negative current (e.g. <5%), and the can may contribute a large percentage of the negative current (e.g. >95%). A substantially monopolar field may be characterized as a field having a can contributing a threshold indicating a relatively high percentage of the current for a given polarity. For example, the threshold may be 75% or may be a percentage between 75% and 100%. Multipolar stimulation uses a multipolar electrode configuration with multiple (two or more) electrodes selected from electrodes within the lead system 208 and none of electrodes) 214. A bipolar electrode configuration generally refers to no current contribution by electrode(s) 214, and monopolar electrode configuration generally refers to all current of given polarity being contributed by electrode(s) 214. However, as will be further discussed below with respect to FIG. 8, the amount of current applied to electrode(s) 214 may be anywhere on a spectrum from none to all of a given polarity.

Figure 3:
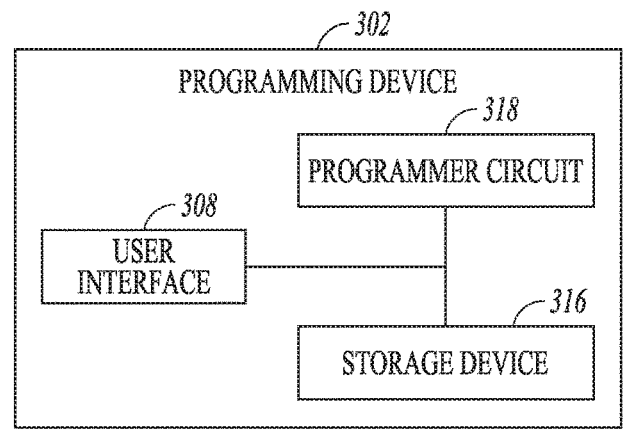
FIG. 3 illustrates, by way of example and not limitation, a programming device, which may be an embodiment of the programming device and implemented in neuromodulation system.

FIG. 3 illustrates, by way of example and not limitation, a programming device 302, which may be an embodiment of the programming device 102 and implemented in neuromodulation system 100. The programming device 302 may include a storage device 316, a programmer circuit 318, and a user interface 308. The programmer circuit 318 may be a part of control circuitry of the programming device 302, and is configured to support one or more functions allowing for programming of neuromodulation devices, such as neuromodulation device 104 including its various embodiments as discussed in this document. In various examples, the programmer circuit 318 may generate a plurality of neuromodulation parameters, collectively referred to as a neuromodulation configuration or neuromodulator settings, that control the delivery of the electrical pulses. In various examples, the neuromodulation configuration may specify a stimulation current (e.g., amplitude or energy of the stimulation) and an electrical current fractionalization across the plurality of electrodes. In some examples, the neuromodulation configuration may include a stimulation location and a stimulation current that corresponds to a metric value. In various examples, the neuromodulation configuration may include a virtual electrode state that specifies a virtual electrode type, location of the virtual electrode in a coordinate space, and stimulation current associated with virtual electrode voltage field and virtual electrode location. Electrical current fractionalization across a plurality of electrodes may be determined based on the voltage field of the virtual electrode.

The storage device 316 may store information used by the programmer circuit 318, including the neuromodulation configuration. The user interface 308 represents an embodiment of user interface 108, and may be coupled to the programmer circuit 318. In various examples, the user interface 308 may allow for definition of a pattern of electrical pulses for delivery during a neuromodulation therapy session by creating and/or adjusting one or more waveforms using a graphical method. The definition may also include definition of one or more neuromodulation fields each associated with one or more pulses in the pattern of electrical pulses. In various examples, the user interface 308 may include a GUI that allows the user to define the pattern pulses and perform other functions using graphical methods.

The circuits or subcircuits included in the neuromodulation system or devices, and their variations discussed in this document, may be implemented using a combination of hardware and software. For example, the circuits may be implemented using an application-specific circuit constructed to perform one or more particular functions or a general-purpose circuit programmed to perform such function(s). Such a general-purpose circuit includes, but is not limited to, a microprocessor or a portion thereof, a microcontroller or portions thereof, and a programmable logic circuit or a portion thereof.

Figure 4:
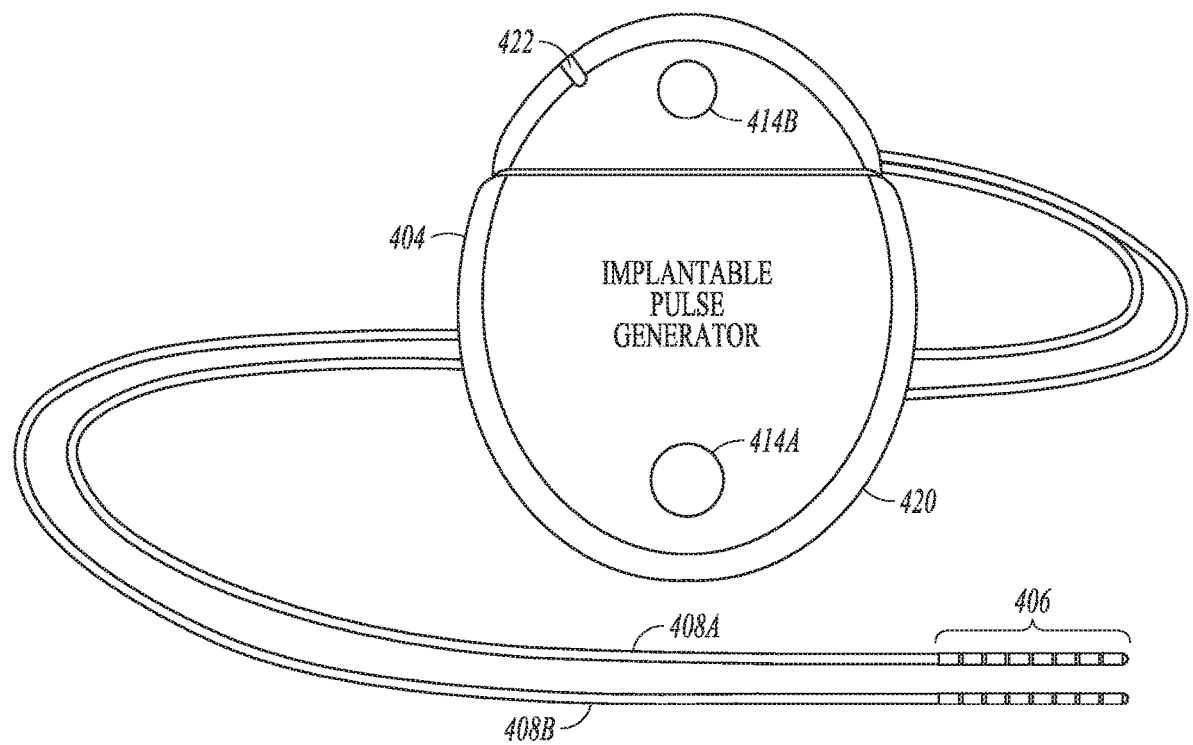
FIG. 4 illustrates, by way of example and not limitation, an embodiment of an implantable pulse generator (IPG) and an implantable lead system.

FIG. 4 illustrates, by way of example and not limitation, an embodiment of an implantable pulse generator (IPG) 404 and an implantable lead system, illustrated as two leads 408A and 408B. The IPG 404 represents an example implementation of neuromodulation device 204, and may include a hermetically-sealed IPG case 420 to house the electronic circuitry of IPG 404. The IPG 404 may include an electrode 414A and may include electrode 414B formed on the IPG case 420. The IPG 404 may include an IPG header 422 for coupling the proximal ends of leads 408A and 408B. Electrodes 414A and/or 414B may each be referred to as a reference electrode or can electrode. The IPG 404 may be communicatively coupled to a programming device, such as the programmer device 102 or the programming device 302, and configured to generate and deliver neuromodulation energy according to the neuromodulator configuration generated by the programming device 102 or 302.

The illustrated lead system includes, by way of example and not limitation, two implantable leads 408A and 408B. As illustrated in FIG. 4, the IPG 404 may be coupled to the implantable leads 408A-B at a proximal end of each lead. The distal end of each lead includes electrical contacts or electrodes 406 for contacting a tissue site targeted for electrical neuromodulation. In various examples, one or more of the electrodes 406 may be column electrodes (also known as ring electrodes), or segmented electrodes circumferentially disposed on a directional lead such as 408A or 408B.

The implantable leads and electrodes may be shaped and sized to provide electrical neuromodulation energy to a neural target, such as a brain, a nerve target of a spinal cord, or a peripheral nerve target. Neuromodulation energy may be delivered in a unipolar mode between an electrode selected from electrodes 406 and another electrode selected from electrodes 414A and 414B, or in a balanced or unbalanced bipolar mode using a pair, or more, of electrodes on the same lead (e.g., lead 408A or lead 408B), with the balancing current being applied to reference electrodes 414A or 414B. Neuromodulation energy may be delivered in an extended bipolar mode using one or more electrodes of a lead (e.g., one or more electrodes of lead 408A) and one or more electrodes of a different lead (e.g., one or more electrodes of lead 408B).

The electronic circuitry of IPG 404 may include a control circuit that controls delivery of the neuromodulator energy. The control circuit may include a microprocessor, a digital signal processor, application specific integrated circuit (ASIC), or other type of processor, interpreting or executing instructions included in software or firmware. The neuromodulation energy may be delivered according to specified (e.g., programmed) modulation parameters. Examples of setting modulation parameters may include, among other things, selecting the electrodes or electrode combinations used in the neuromodulation, configuring an electrode or electrodes as the anode or the cathode for the neuromodulation, and specifying pulse parameters. Examples of pulse parameters include, among other things, the amplitude of a pulse (specified in current or voltage), pulse duration (e.g., in microseconds), pulse rate (e.g., in pulses per second), and parameters associated with a pulse train or pattern such as burst rate (e.g., an "on" modulation time followed by an "off" modulation time), amplitudes of pulses in the pulse train, polarity of the pulses, etc.

The modulation parameters may additionally include fractionalization across electrodes. The fractionalization specifies distribution (e.g., the percentage) of the neuromodulation current, voltage, or electrical energy provided by an electrode or electrode combination, which affect the spatial distribution of the resultant neuromodulation field. In an example, current fractionalization specifies percentage cathodic current, percentage anodic current, or off (no current allocation). Current may be fractionalized across the active electrodes, such that active electrodes may receive a respective current percentage. Non-active electrodes are "off" or contribute no current to the neuromodulation. In the monopolar case, the fractionalized currents across the active electrodes add up to 100%. In the bipolar or multipolar cases, the fractionalized currents for at least one polarity add up to 100%, with any remaining percentage being allocated to the reference electrodes. Control of the current in terms of percentage allows precise and consistent distribution of the current among the electrodes even as the overall current amplitude for the parameter set is adjusted. In some examples, the current fractionalization may be defined by assigning an absolute current value (e.g., in milliampere, or mA) rather than a percentage to each electrode. Control of the current in terms of absolute values allows precise dosing of current through each specific electrode. It is suited for changing the current one contact at a time (and allows the user to do so) to shape the neuromodulation like a piece of clay (pushing/pulling one spot at a time).

The current fractionalization takes into account electrode/tissue coupling differences, which are the differences in how the tissue underlying each electrode reacts to electrical neuromodulation. In addition, electrodes on the distal portion of the lead may have lower gradient in the longitudinal direction, as electrical field strength may taper down at the ends of the lead. Current fractionalization may accommodate variation in the tissue underlying those electrodes. Various embodiments described herein implement a programmed algorithm to determine the appropriate fractionalization to achieve a desired neuromodulation field property.

Figure 5:
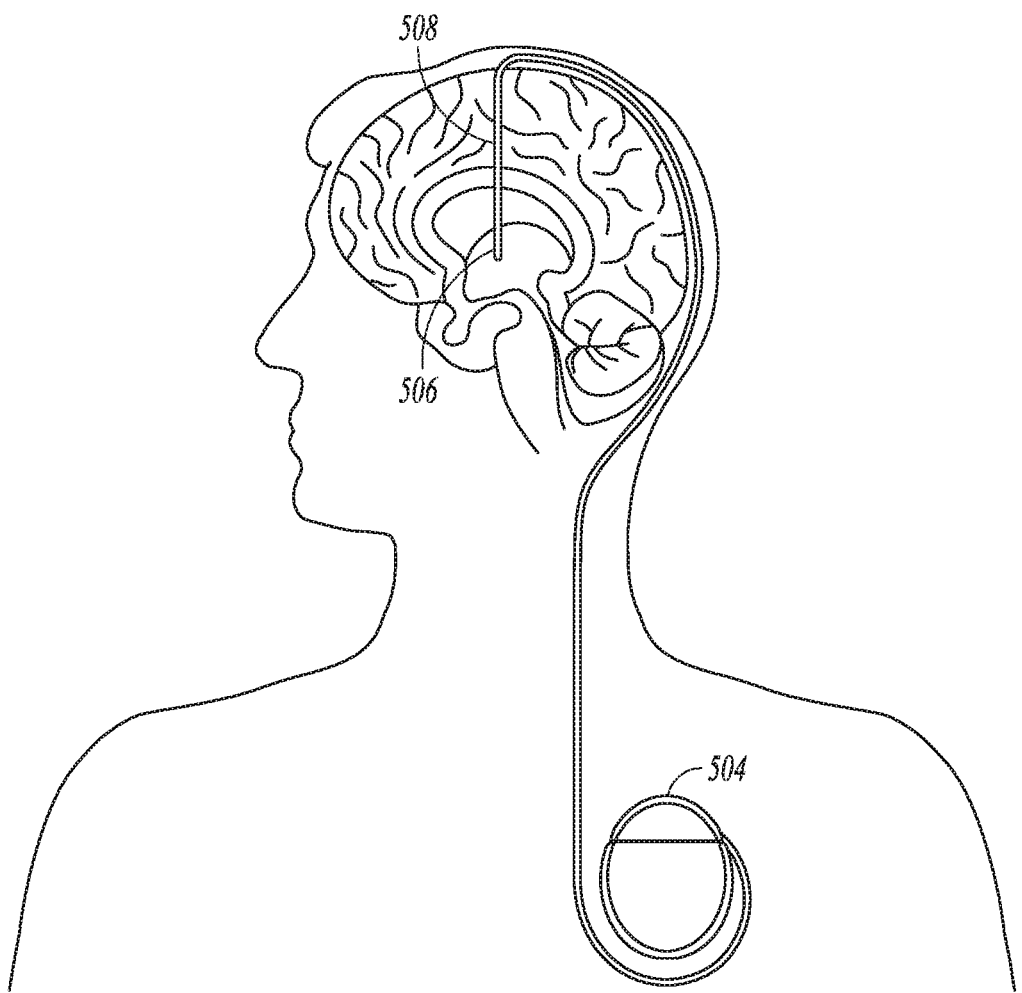
FIG. 5 illustrates, by way of example and not limitation, an embodiment of an IPG and an implantable lead system arranged to provide brain neuromodulation to a patient.

FIG. 5 illustrates, by way of example and not limitation, an embodiment of an IPG 504 and an implantable lead system 508 arranged to provide brain neuromodulation to a patient. An example of IPG 504 includes the LPG 404. The lead system 508 may include electrodes 506. An example of lead system 508 includes one or more of the leads 408A-B. An example of the electrodes 506 includes at least a portion of the electrodes 406. In the illustrated example, the IPG 504 and the implantable lead system 508 may provide DBS to a patient, with the neuromodulation target being neuronal tissue in a subdivision of the thalamus of the patient's brain. Other examples of DBS targets include neuronal tissue of the globus pallidus (GPi), the subthalamic nucleus (STN), the pedunculopontine nucleus (PPN), substantia nigra pars reticulate (SNr), cortex, globus pallidus externus (GPe), medial forebrain bundle (MFB), periaquaductal gray (PAG), periventricular gray (PVG), habenula, subgenual cingulate, ventral intermediate nucleus (VIM), anterior nucleus (AN), other nuclei of the thalamus, zona incerta, ventral capsule, ventral striatum, nucleus accumbens, white matter tracts connecting these and other structures. The DBS targets may also include regions determined analytically based on side effects or benefits observed in one or more patients, as well as regions specified by the user.

Figure 6:
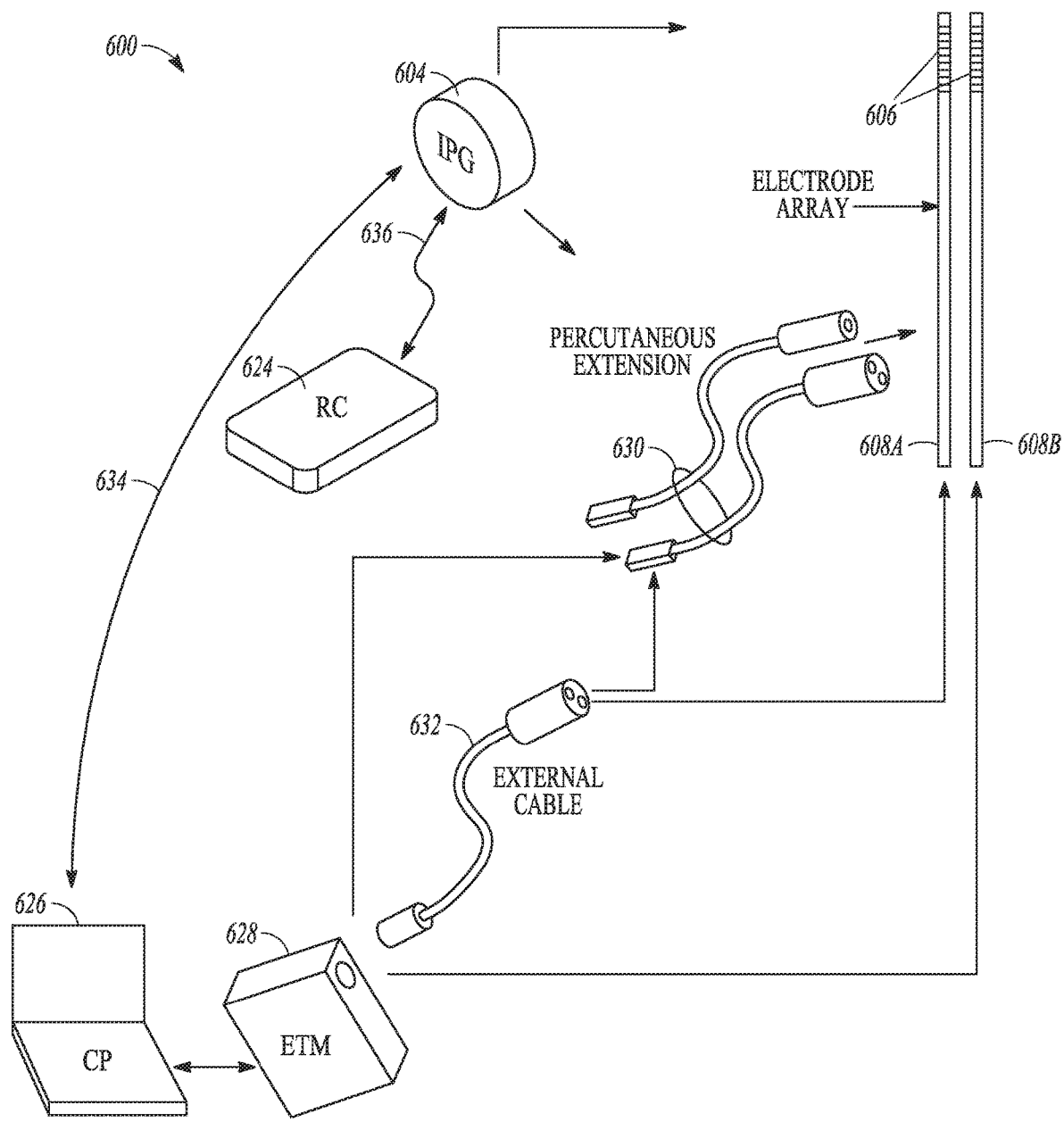
FIG. 6 illustrates, by way of example and not limitation, an embodiment of portions of a neuromodulation system.

FIG. 6 illustrates, by way of example and not limitation, an embodiment of portions of a neuromodulation system 600. The system 600 includes an IPG 604, implantable neuromodulation leads 608A and 608B, an external remote controller (RC) 624, a clinician's programmer (CP) 626, and an external trial modulator (ETM) 628. The system 600 may additionally include external sensors configured to sense one or more physiological parameters, such as a heart rate sensor, a pulse oximeter, an electrocardiogram sensor, an inertial sensor, or an electroencephalogram sensor, among others. The IPG 604 may be electrically coupled to the leads 608A and 608B directly or through percutaneous extension leads 630. The ETM 634 may be electrically connectable to the leads 608A and 608B via one or both of the percutaneous extension leads 630 and/or the external cable 632. The system 600 represents an embodiment of system 100, with IPG 604 representing an embodiment of the neuromodulation device 104, electrodes 606 of leads 608A and 608B representing the electrodes 106, and CP 626, RC 624, and the ETM 628 collectively representing the programming device 102.

The ETM 628 may be standalone or incorporated into the CP 630. The ETM 628 may have similar pulse generation circuitry as IPG 604 to deliver neuromodulation energy according to specified modulation parameters as discussed above. in an example, the ETM 628 is an external device and may be used as a preliminary stimulator after leads 408A and 408B have been implanted and used prior to stimulation with IPG 604 to test the patient's responsiveness to the stimulation that is to be provided by IPG 604. An external ETM 634 may be more easily configurable than the IPG 604.

The CP 626 may configure the neuromodulation provided by the ETM 628. If the ETM 628 is not integrated into the CP 626, then the CP 626 may communicate with ETM 628 using a wired connection (e.g., over a USB link) or by wireless telemetry such as using a wireless communications link. The CP 626 may also communicate with IPG 604 using a wireless communications link 634.

An example of wireless telemetry is based on inductive coupling between two closely-placed coils using the mutual inductance between these coils. This type of telemetry is referred to as inductive telemetry or near-field telemetry because the coils must typically be closely situated for obtaining inductively coupled communication. The IPG 604 may include the first coil and a communication circuit. The CP 626 may include or be otherwise electrically connected to the second coil such as in the form of a wand that may be place near the IPG 604. Another example of wireless telemetry includes a far-field telemetry link, also referred to as a radio frequency (RF) telemetry link. A far-field, also referred to as the Fraunhofer zone, refers to the zone in which a component of an electromagnetic field produced by the transmitting electromagnetic radiation source decays substantially proportionally to 1/r, where r is the distance between an observation point and the radiation source. Accordingly, far-field refers to the zone outside the boundary of $r=\lambda/2\pi$, where $\lambda$ is the wavelength of the transmitted electromagnetic energy. In one example, a communication range of an RF telemetry link is at least six feet but may be as long as allowed by the particular communication technology. RF antennas may be included, for example, in the header of the IPG 604 and in the housing of the CP 630, eliminating the need for a wand or other means of inductive coupling. An example is such an RF telemetry link is a Bluetooth® wireless link.

The CP 626 may be used to set modulation parameters for the neuromodulation after the IPG 604 has been implanted. This allows the neuromodulation to be tuned if the requirements for the neuromodulation change after implantation. The CP 626 may also upload information from or download information to the IPG 604.

The RC 624 also communicates with the IPG 604 using a wireless link 636. The RC 624 may be a communication device used by the user or given to the patient. The RC 624 may have reduced programming capability compared to the CP 626. This allows the user or patient to alter the neuromodulation therapy but does not allow the patient full control over the therapy. For example, the patient may be able to increase the amplitude of neuromodulation pulses or change the time that a preprogrammed stimulation pulse train is applied. The RC 624 may be programmed by the CP 626. The CP 626 may communicate with the RC 624 using a wired or wireless communications link. In some embodiments, the CP 626 is able to program the RC 624 when remotely located from the RC 624. In some examples, the RC 624 may download data to and upload data from the IPG 604.

Figure 7:
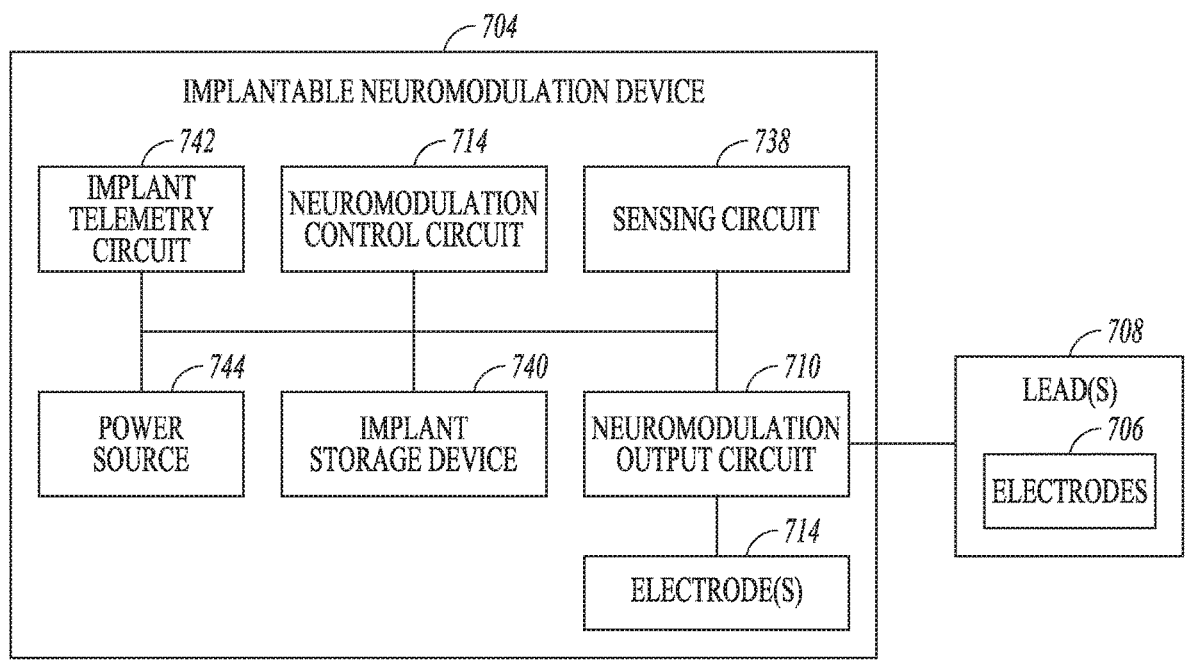
FIG. 7 illustrates, by way of example and not limitation, an embodiment of implantable neuromodulation device and one or more leads of an implantable neuromodulation system, such as the implantable system.

FIG. 7 illustrates, by way of example and not limitation, an embodiment of implantable neuromodulation device 704 and one or more leads 708 of an implantable neuromodulation system, such as the implantable system 600. The implantable neuromodulation device 704 represents an embodiment of stimulation device 104 or 204 and may be implemented, for example, as the IPG 604. Lead(s) 708 represents an embodiment of lead system 208 and may be implemented, for example, as implantable leads 608A-B. The lead(s) 708 includes electrodes 706, which represents an embodiment of electrodes 106 or 206 and may be implemented as electrodes 606. In some examples, the implantable stimulator 704 may additionally be communicatively coupled to one or more external sensors configured to sense one or more physiological parameters, such as a heart rate sensor, a pulse oximeter, an electrocardiogram sensor, an inertial sensor, or an electroencephalogram sensor, among others.

The implantable neuromodulation device 704 may include a sensing circuit 738 when the stimulator needs a sensing capability, neuromodulation output circuit 710, a neuromodulator control circuit 712, an implant storage device 740, an implant telemetry circuit 742, a power source 744, and one or more electrodes 714. The sensing circuit 738, when included, may be configured to sense one or more physiologic signals for purposes of patient monitoring and/or feedback control of the neuromodulation. Examples of the physiologic signals include neural and other signals each indicative of a condition of the patient that is treated by the neuromodulation and/or a response of the patient to the delivery of the neuromodulation. The stimulation output circuit 212 is electrically connected to electrodes 706 through one or more leads 708 as well as electrodes 707, and delivers each of the neuromodulation pulses through a set of electrodes selected from electrodes 706 and electrode(s) 707. The device control circuit 714 represents an embodiment of device control circuit 214, and controls the delivery of the pulses according to the stimulation configuration (including stimulation parameters) received from the programming device 102 or 302. In one embodiment, the device control circuit 714 controls the delivery of the pulses using the one or more sensed physiologic signals. The implant telemetry circuit 744 provides the implantable stimulator 704 with wireless communication with another device, such as the CP 630 or the RC 632, including receiving values of the plurality of stimulation parameters from the other device. The implant storage device 746 stores the received stimulation configuration, including values of the plurality of stimulation parameters. The power source 748 provides the implantable stimulator 704 with energy for its operation. The power source 748 may include a battery. In one embodiment, the power source 748 includes a rechargeable battery and a battery charging circuit for charging the rechargeable battery. The implant telemetry circuit 744 may also function as a power receiver that receives power transmitted from an external device through an inductive couple. The electrode(s) 714 allow for delivery of the pulses in the monopolar mode or unbalanced bipolar mode. Examples of the electrode(s) 714 include electrode 414A and electrode 414B in IPG 404 as illustrated in FIG. 4.

In an example, the implantable neuromodulation device 704 may be used as a master database. A patient implanted with implantable stimulator 704 (such as may be implemented as IPG 604) may therefore carry patient information needed for his or her medical care when such information is otherwise unavailable. The implant storage device 740 may be configured to store such patient information. For example, the patient may be given a new RC 632 and/or travel to a new clinic where a new CP 630 is used to communicate with the device implanted in him or her. The new RC 632 and/or CP 630 may communicate with the implantable stimulator 704 to retrieve the patient information stored in implant storage device 740 through the implant telemetry circuit 744 and the wireless communication link 640, and allow for any necessary adjustment of the operation of the implantable stimulator 704 based on the retrieved patient information. The patient information stored in the implant storage device 746 may include, for example, various types of neuromodulation settings. Examples may include positions of lead(s) 708 and electrodes 706 relative to the patient's anatomy (transformation for fusing computerized tomogram (CT) of post-operative lead placement to magnetic resonance imaging (MRI) of the brain), clinical effect data, objective measurements using quantitative assessments of symptoms (e.g., using micro-electrode recording, accelerometers, and/or other sensors), and/or other information considered important or useful for providing adequate care for the patient. In various examples, the patient information to be stored in implant storage device 740 may include data transmitted to implantable stimulator 704 for storage as part of the patient information and data acquired by implantable stimulator 704, such as by using sensing circuit 742.

Figure 8:
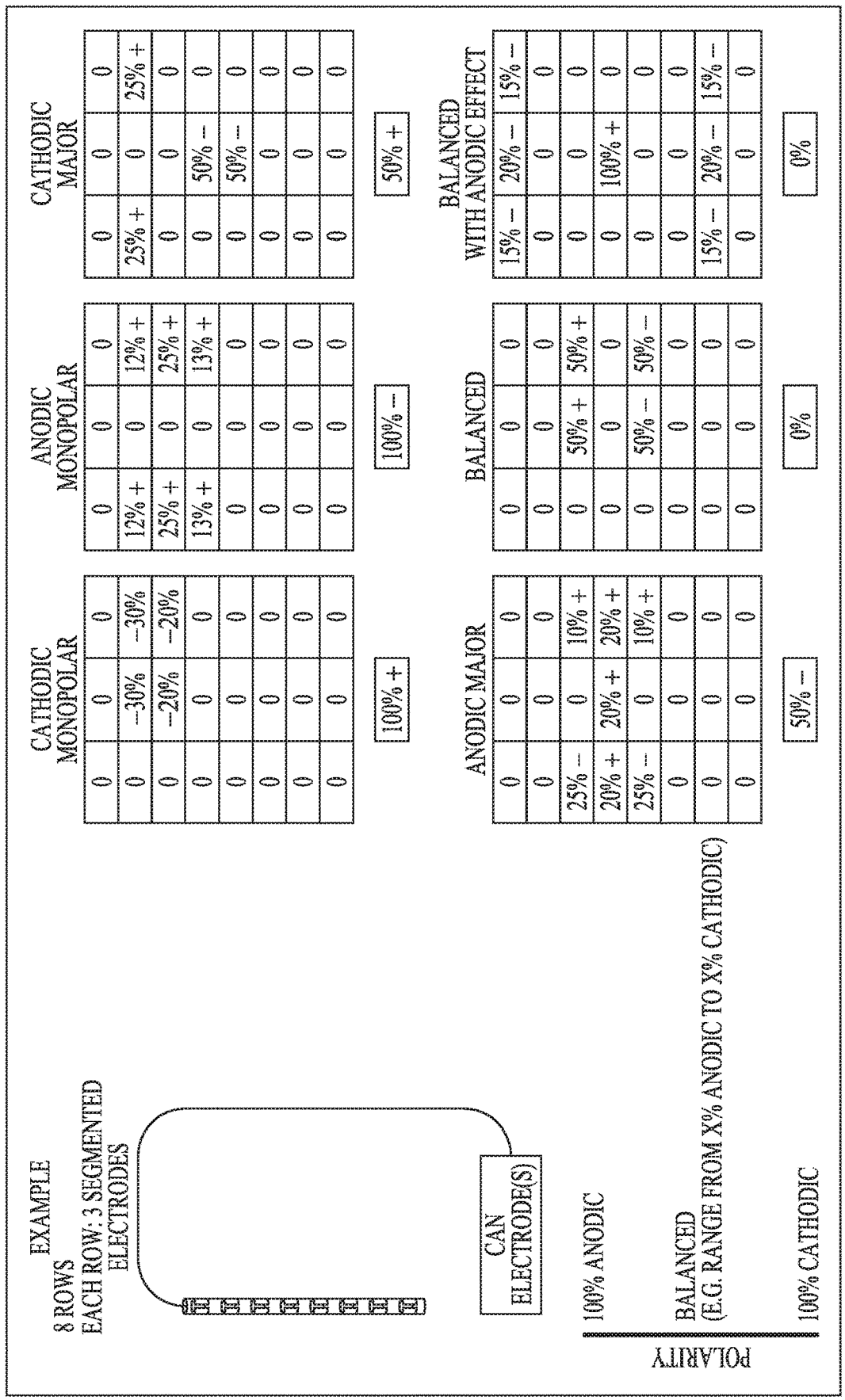
FIG. 8 illustrates examples of fractionalizations to provide different modulation types.

FIG. 8 illustrates examples of fractionalizations to provide different modulation types. The neuromodulation device includes an IPG with a can electrode, and a lead with 8 sets or rows of electrodes, where each set or row includes 3 fractionalized electrodes distributed around the lead (e.g. at 0°, 120° and 240). The figure illustrates six tables that have 8 rows and 3 columns. Each table represents the lead electrodes, such that each cell in the table represents one of the electrodes on lead, and the cell below the table represents a can electrode. The data within the cells is intended to illustrate fractionalization values for the electrodes. The total positive charge (anodic) will equal the total negative charge (cathodic) in the system. However, up to 100% of the anodic or cathodic contribution may be provided by the can electrode. As such, the polarity of the modulation field at the targeted region(s) may be 100% cathodic (conventional monopolar DBS neuromodulation), 100% anodic (anodic monopolar), mostly cathodic (e.g. cathodic major), mostly anodic (anodic major), or balanced such as may occur if there is no current contribution by the can or other reference electrode). It may be possible to provide balanced polarity in so far as the can electrode is not providing a current contribution, but the current contributions for one polarity is spread across many electrodes and the current contributions for the other polarity is provided by one or a few electrodes. Thus, it may be possible to provide a balanced modulation using the lead electrodes, but still provide an anodic effect for a particular targeted region.

The polarity of the modulation field at the lead electrodes (illustrated by the values within the table cells) may be 100% anodic (no cathodic contribution), 100% cathodic (no anodic contribution), balanced (anodic contribution equals cathodic contribution), approximately or nearly balanced (anodic contribution is within +/−X % of cathodic contribution; such as 45%:50% or 50%:45% if X=5). To be characterized as relatively balanced, a relatively small percentage (X % where X=10 or less by way of example) of the cathodic or anodic contribution may be provided by the can electrode. As identifier earlier, the polarity of the field may also be considered substantially monopolar or pseudo-monopolar if the can is contributing a relatively larger percentage of the current (e.g. 90% or higher). The present subject matter is not limited to these values, as the system is capable of using the lead electrodes to provide anywhere from 0 to 100% of the total anodic energy, or using the lead electrodes to provide anywhere from 0 to 100% of the total cathodic energy. If something is anodic major, the anodic contribution of the lead electrodes sums to 100%, but the cathodic contribution of the lead electrodes sums to less than 100%. Similarly, cathodic major indicates that the cathodic contribution of the lead electrodes sums to 100%, but the anodic contribution of the lead electrodes sums to less than 100%.

These fractionalizations and neuromodulation types, or combination of neuromodulation types, may be stored as neuromodulation settings for a programmed neuromodulation therapy. Other information that may be stored as neuromodulation parameter settings may include clinical effects, targeted region(s), and avoidance region(s), if any, to particular neuromodulation parameter settings (e.g. amplitude, pulse width, fractionalization, polarity).

Various system embodiments may be capable of operating in multiple neuromodulation modes, such as one or more of anodic, cathodic, balanced, or other mixtures of anodic/cathodic modulation field polarities. For example, when the system in placed in anodic mode, the system may be configured to automatically enable steering of an anodic field. Similarly, when the system in placed in cathodic mode, the system may be configured to automatically enable steering of an cathodic field. Other features/algorithms may be affected by the mode. For example, one type of stimulation field model (SFM) algorithm may be used in anodic mode, and a different type of SFM may be used in cathodic mode. In hybrid modes, the SFMs of anodic type may be distinguished from SFMs of cathodic type (or local cell vs axon of passage types) using distinct coloring, even if shown simultaneously. Default settings of other parameters may be mode-specific. By way of example and not limitation, a default pulse width may be 30 microseconds in cathodic mode and may be 100 microseconds in anodic mode.

Figure 9:
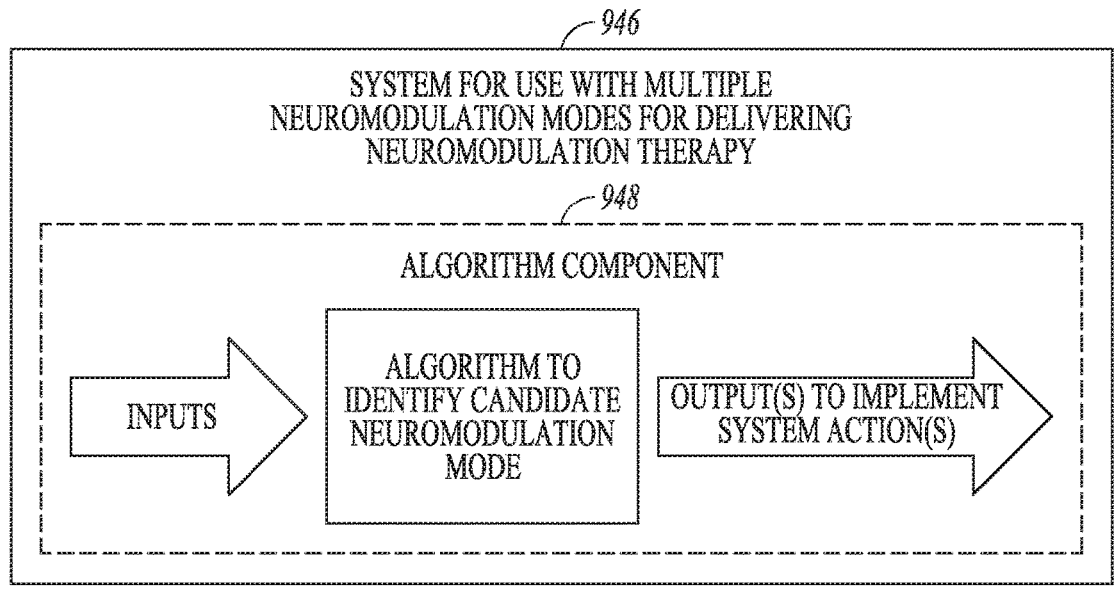
FIG. 9 illustrates an embodiment of a system for use with multiple neuromodulation modes for delivering neuromodulation therapy.

FIG. 9 illustrates an embodiment of a system for use with multiple neuromodulation modes for delivering neuromodulation therapy. As will be discussed in more detail below, the illustrated system 946 includes an algorithm component 948 that implements an algorithm on received input(s) to produce system output(s). The illustrated system may be implemented with a neuromodulation system such as illustrated previously, and more particularly may be implemented with a system that is capable of delivering multiple neuromodulation modes.

Figure 10:
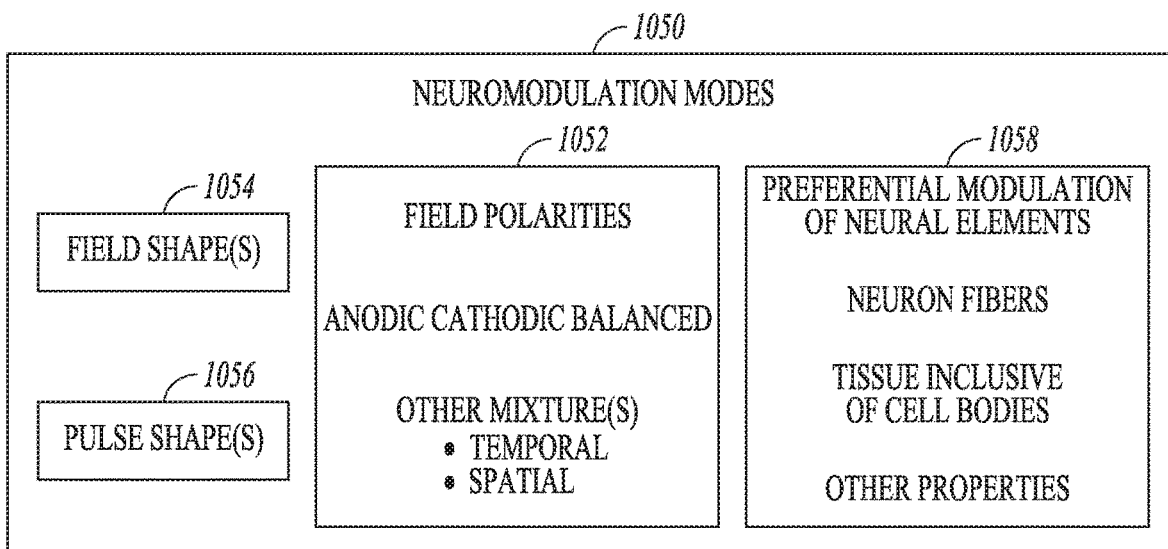
FIG. 10 illustrates examples of neuromodulation modes that may be included, according to various embodiments, within the multiple neuromodulation modes capable of being delivered by the system of FIG. 9.

FIG. 10 illustrates examples of neuromodulation modes 1050 that may be included, according to various embodiments, within the multiple neuromodulation modes capable of being delivered by the system of FIG. 9. The modes 1050 may include one or more of anodic, cathodic, balanced, or other mixtures of anodic/cathodic modulation field polarities 1052. The mixed anodic/cathodic neuromodulation may be delivered using a temporal mix (e.g. anodic for first time and cathodic for a second time) or spatial mix (anodic in a first portion of the lead electrodes, and cathodic in a second portion of lead electrodes). For example, a mixed polarity type may be provided as a hybrid mode in either space (e.g. field shape) or time (e.g. pulse shape, or pulse schedule or both) along a mode dimension axis. The modes 1050 may include one or more modulation field shapes 1054, or one or more pulse shapes 1056. In some embodiments, the modes 1050 preferentially modulate some neural elements over other neural elements 1058. For example, some embodiments may preferentially modulate neuron fibers, and some embodiments may preferentially modulate tissue inclusive of cell bodies. Neural elements may be preferentially modulated based on other properties of the neural elements.

Figure 11A:
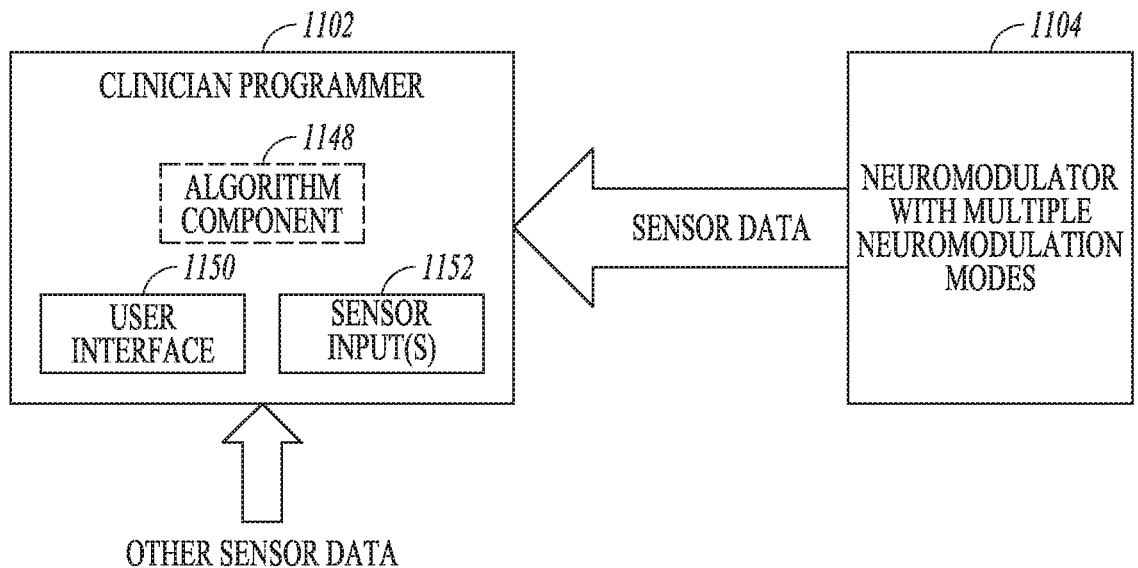
FIGS. 11A-11C illustrates various system embodiments with different portions of the system implementing the algorithm.
Figure 11B:
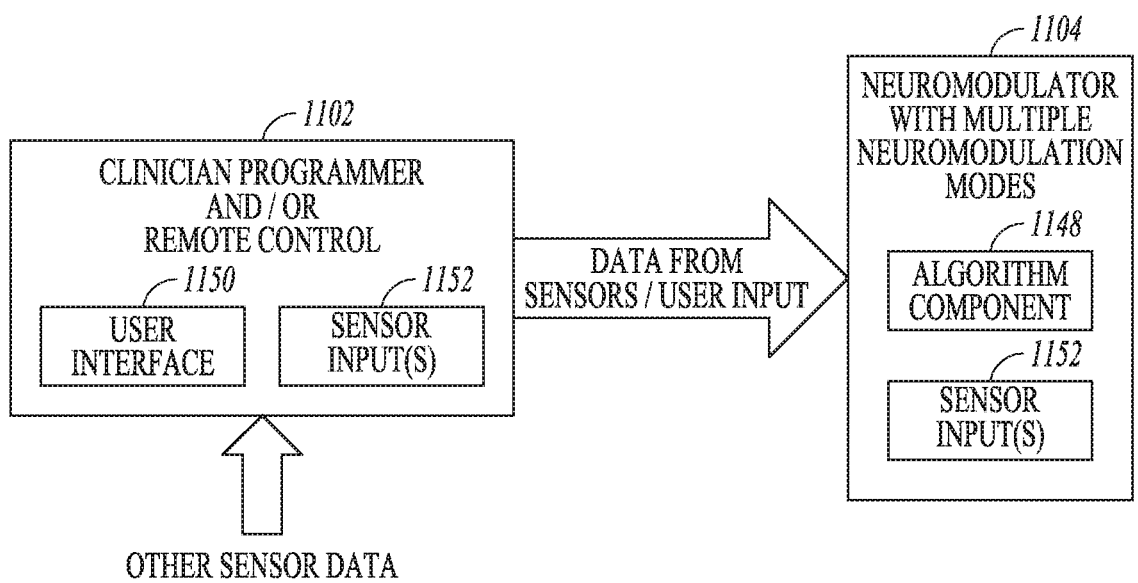
Figure 11C:
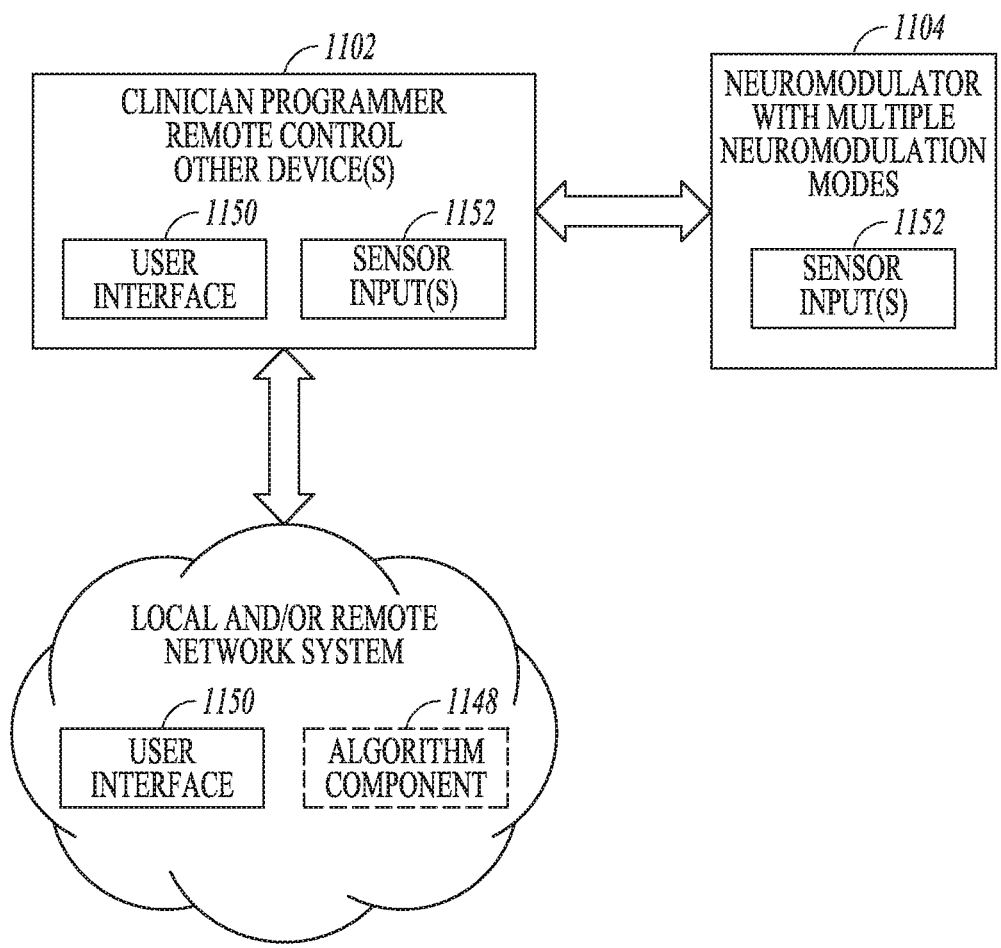

FIGS. 11A-11C illustrates various neuromodulation system embodiments with different portions of the system implementing the algorithm. The neuromodulation system includes a neuromodulator 1104 (e.g. an implantable neuromodulator device similar to device 104 illustrated in FIG. 1, device 2014 illustrated in FIG. 2, device 404 illustrated in FIG. 4, and device 504 illustrated in FIG. 5) and a clinician programmer, remote control or other device 1102 (e.g. a programming device similar to the device 102 illustrated in FIG. 1 and device 302 illustrated in FIG. 3). A user interface 1150 may be used to receive user inputs, which may be used to receive user-inputted information such as user-inputted disease, a user-inputted disease state, a user-inputted symptom-related information, or a user-inputted physical state or mental state or time. More than one user interface may be used within a network environment to receive the user-inputted information. Sensor inputs 1152 may be used to receive sensor data or information regarding sensor data. The sensor data may include sensor data regarding impedance, sensor data regarding brain activity, sensor data regarding activity in the spinal cord, dorsal horn or dorsal root, or sensor data regarding physical activity or physical state. Sensor inputs may be received by the neuromodulator 1104 and/or other devices 1102. Some system embodiments additionally include components, such as servers or other devices within a local and or remote network and/or cloud-based services over the internet. The algorithm component 1148 may be implemented by the clinician programmer or remote control, (FIG. 11A), the neuromodulator (FIG. 11B), or by components within the local and or remote network (FIG. 11C). The algorithm may also be distributed across two or more processors within the system.

Figure 12:
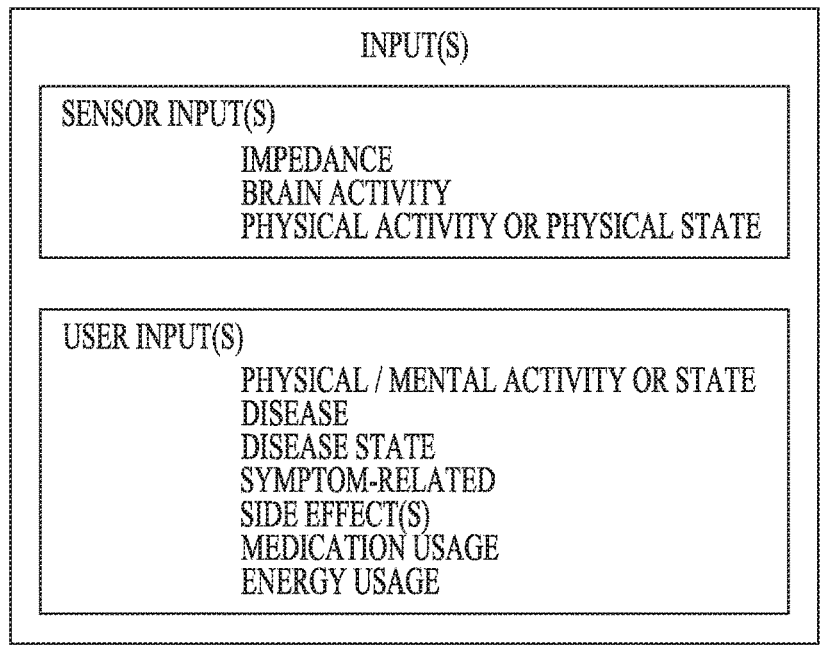
FIG. 12 illustrates examples of inputs to the algorithm component illustrated in FIG. 9.

FIG. 12 illustrates examples of inputs to the algorithm component illustrated in FIG. 9. The algorithm inputs may include sensor inputs or user inputs. Candidate inputs include one or more of a disease type, symptoms, disease stage, stimulation-induced side effects, energy usage, and medication usages. Examples of diseases that may be candidate inputs include Parkinson's disease, essential tremor, dystonia, Alzheimer's, stroke, major depressive disorder, bipolar depression, obsessive-compulsive disorder (OCD), pain, epilepsy, obesity, addiction, and the like.

The symptoms of the disease may represent the presence or level of the disease. By way example, symptoms of Parkinson's disease may include bradykinesia, rigidity, tremor, freezing of gait, gait, axial symptoms, dementia, and dyskinesias. Examples of disease stage inputs for Parkinson's disease may include mild, moderate, severe, unified Parkinson's disease rating scale (UPDRS) or a subset (e.g. UPDRS III) or a portion (e.g. MDS-UPDRS), Hoehn & Yahr, and medication resistant. Examples of stimulation-induced side effects, which may be beneficial for follow-up programming, may include cognition, oculomotor, dysarthria, paresthesia, and the like. Energy usage information may include the ability to charge a rechargeable device, the amount of charging time that is considered to be acceptable, a minimum expected device longevity for a patient, and the like. Medication usage may provide an indication of disease progression or treatment. Medicinal treatments may affect the underlying neural network, and change how they are affected by various types of modulation types.

The present subject matter may be particularly beneficial for neurodegenerative diseases, as the neural network is always changing as the disease progresses. For example, some neuromodulation systems that treat Parkinson's disease may make a determination of neuromodulation mode (e.g. anodic or cathodic or mixed neuromodulation) based on a determination that the patient is rigidity dominant, without a high level of tremor. In another example, neuropathic pain may be the disease, and the symptoms may include the location of the pain and/or a pain score based on a pain scale such as a visual analog pain scale.

Some embodiments provide a close loop system for automatic selection neuromodulation polarity type. The system may identify triggers for switching the between the neuromodulation polarity type. An example includes triggering a polarity switch from a detected patient state based on one or more smart appliances. Therefore, the sensor that provides the at least one sensor input to the algorithm may include at least one of a sensor of impedance, a sensor of brain activity, a sensor of activity in the spinal cord, dorsal horn or dorsal root, or a sensor of physical or mental activity or state. The use of sensor-based inputs may be useful in removing the need for manual intervention to better optimize therapy for a patient and improve programming time.

The sensor of physical or mental activity or state may include external or internal sensors such as heart rate, blood pressure, pulse oximeter, activity, respiration, sweat, sleep and posture sensors. Any other sensor capable of producing a signal based on the patient's physical state may be used. Additionally or alternatively, the sensor may include a time of day or user input. These sensors may be useful in clinical, home and other environments. Some other examples of sensors include camera, heat sensors, video sensor, watches, audio (e.g. speech) sensors. Some embodiments may use smart appliance(s) as an input for recognizing patient state.

Some embodiments may detect brain activity (e.g. electrode matching and matching local field potential (LFP) spectrum). For example, the systems may be looking for markers for patient conditions that would prefer a particular neuromodulation therapy mode. Also, energy may be saved if anodic neuromodulation is delivered only when indicated, as anodic neuromodulation generally requires more energy than cathodic neuromodulation. For example, if motor activity is sensed, some embodiments may deliver modulation to avoid the side effect.

Some embodiments may use impedance or compliance measurements as an indicator of patient state. For example, actions may be associated with times of day and impedances for those times of day. As such, some embodiments may match impedance to an impedance associated with a time of day to determine the activity associated with the time of day. Impedance changes may also provide information about the physical activity or state of the patient.

Figure 13:
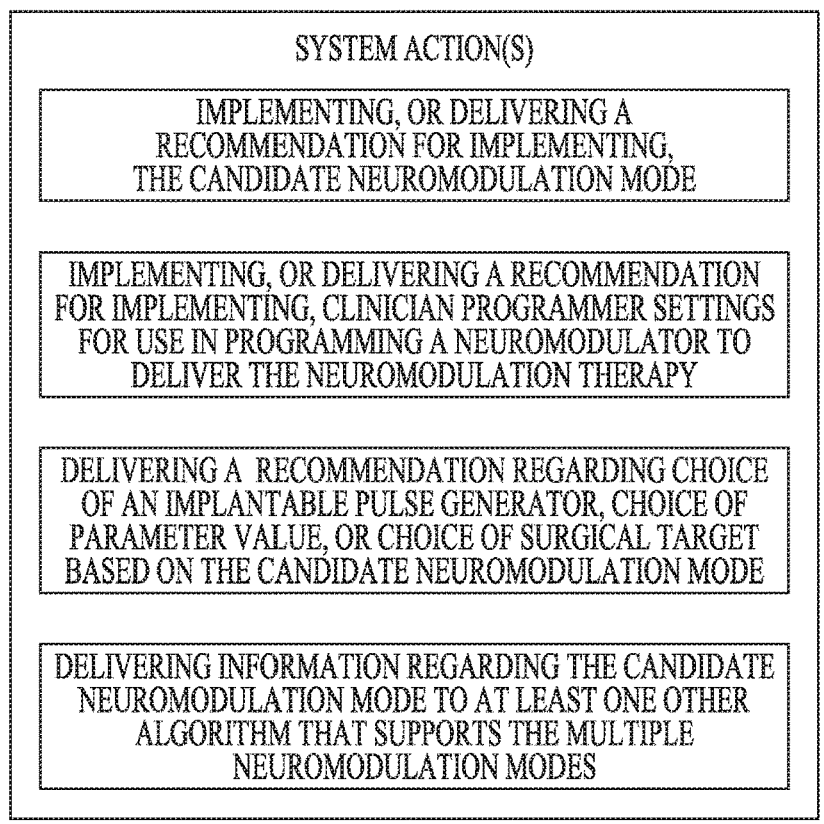
FIG. 13 illustrates examples of outputs from the algorithm component illustrated in FIG. 9.

FIG. 13 illustrates examples of outputs from the algorithm component illustrated in FIG. 9. Candidate outputs may include default settings or user recommendations for a programmer, such as a clinician programmer or remote control. The default settings may relate to a stimulation mode (e.g. anodic, cathodic or mixed). The user recommendations may be delivered via text, voice, graphics, visuals, and the like. By way of example, the candidate outputs may include a default steering mode, default case polarity, default clinical effects map mode, default stimulation field model settings or mode, default target volume(s) settings/mode/ default probabilistic atlas mode/settings, default closed-loop algorithm settings/mode (such as anodic or cathodic kinesia StimPoint (KSP), default anatomy/guide setting/mode; default Boston Scientific's DBS Illumina mode/settings, default modulation signal parameters such as pulse width, frequency, and the like), default pulse settings (continuous variable), or default field/pulse shape scheduling. KSP is an optimization system that includes an algorithm that receives as inputs the stimulation parameters, and the clinical effects associated with those parameters (either input manually or measured with accelerometers and validated methods that are part of KSP), and provides as outputs the next recommended settings to evaluate, and whether or not stopping criteria have been met. DBS Illumina is an inverse algorithm that takes as inputs the position of the lead with respect to a physiological target, and determines an estimate of the fractionalizations and other stimulation parameters that will modulate the physiological target. Additional information may be found in U.S. patent application Ser. No. 15/902,163, filed Feb. 22, 2018, and entitled "Method and Apparatus For Clinical Effects-Based Targeting of Neurostimulation"; and U.S. Provisional Patent Application No. 62/598,558, filed Dec. 14, 2017, and entitled "Systems and Methods for Clinical Effect-Based Neurostimulation". U.S. patent application Ser. No. 15/902,163 and U.S. Provisional Patent Application No. 62/598,558 are hereby incorporated by reference in their entirety.

Some candidate outputs may include inputs to another algorithm (e.g. "next layer algorithm") that also supports such multiple therapy stimulation modes. Examples of such algorithms include KSP-2 (representing a subsequent generation of KSP that uses multiple stimulation modes that may, by way of example, explore both anodic and cathodic monopolar stimulation or other modes), DBS-Illumina 2 (representing a subsequent generation of DBS Illumina that uses multiple stimulation modes that may, by way of example, explore both cell and fiber stimulation or other modes), fully implantable, closed-loop algorithms (based on local field potential, accelerometers, etc.), Guide including SFMs, anatomy, and targets/probabilistic maps. GUIDE is an algorithm that estimates modulation based on input stimulation parameters, and in one embodiment can display that estimate relative to the lead and anatomy. GUIDE can vary the display as parameters are changed. A second generation of GUIDE may include a mode that shows cell modulation and a separate mode that shows fiber modulation.)

Figure 14:
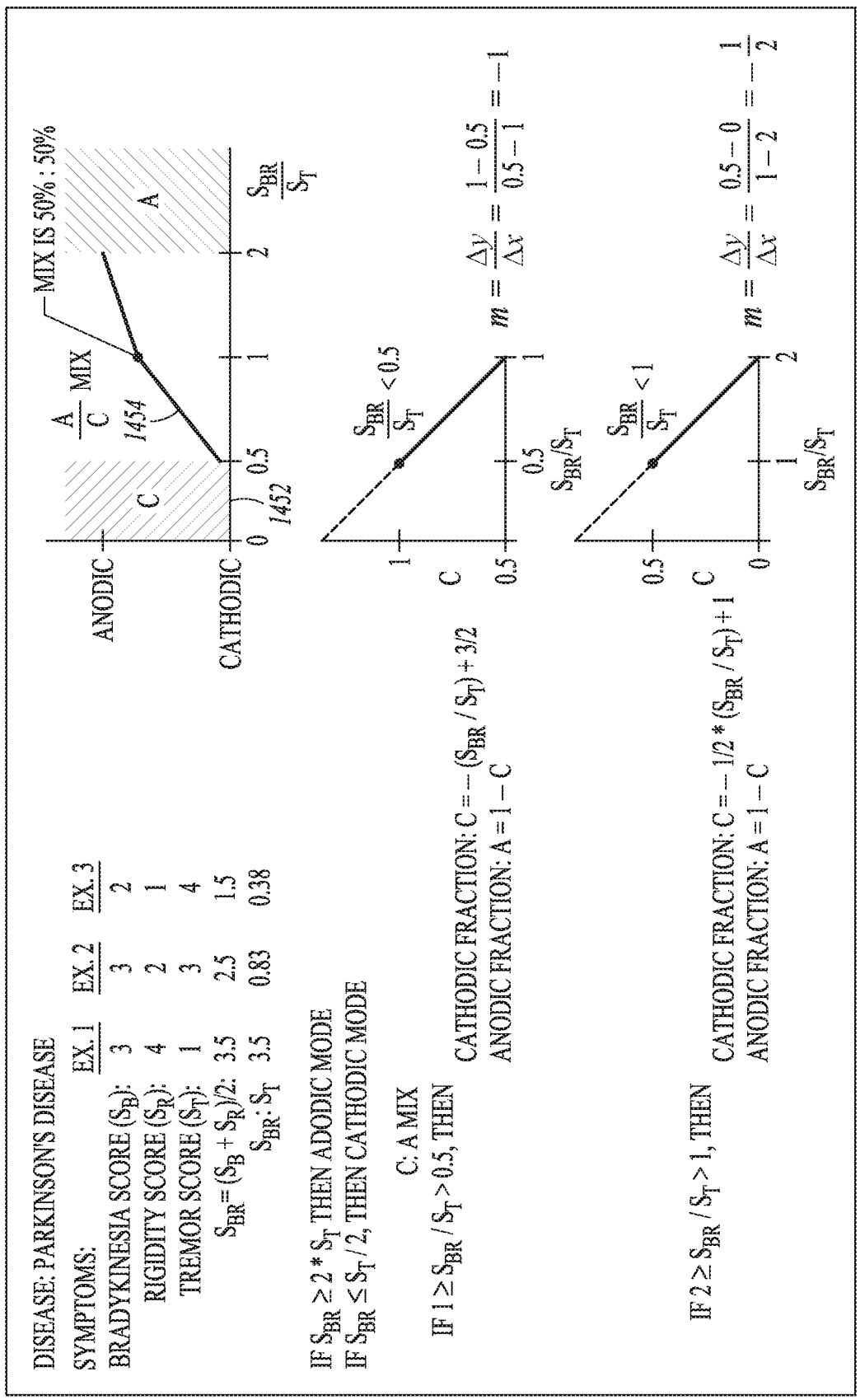
FIG. 14 illustrates an example of an algorithm component.

Candidate outputs may include information useful for choosing a type of implantable pulse generator, likely parameter choice, or surgical target. Examples of such information include mode availability, battery recharge interval, battery longevity, parameters such as pulse width, frequency, expected preferred surgical target. FIG. 14 illustrates an example of an algorithm component. The illustrated algorithm is specific example for Parkinson's disease. Thus, a user input may receive a user-inputted indication that the disease being treated is Parkinson's disease, and may further provide scores for one or symptoms (e.g. Bradykinesia, Ridigity, and Tremor) of Parkinson's disease. The illustrated example in FIG. 14 provides three example sets of scores (Ex. 1, Ex. 2 and Ex. 3) For example, a user may enter a score between 1 and 4 for each of these symptoms. A score ($S_{BR}$) that generally corresponds to the bradykinesia and rigidity (e.g. the average of the bradykinesia and rigidity scores) may be compared to a tremor score ($S_T$) to estimate an appropriate type of neuromodulation. That is, a ratio of $S_{BR}$ to $S_T$ may be used to determine the suggested type of neuromodulation (e.g. anodic, cathodic or mixed). For example, if the average score of the bradykinesia and rigidity $S_{BR}$ is more than twice the score of tremor $S_T$, then anodic neuromodulation may be suggested. If the average score of the bradykinesia and rigidity $S_{BR}$ is less than half of the score of tremor $S_T$, then cathodic neuromodulation may be suggested. Otherwise, a mixture of anodic and cathodic neuromodulation may be suggested. The mixture may be delivered using temporal or spatial techniques. Some embodiments may provide different mixtures based on the score. For example, if a ratio of the average score of the bradykinesia and rigidity $S_{BR}$ to the score of tremor $S_T$ is less than 1 and more than ½, then the cathodic neuromodulation may be determined based on $3/2-S_{BR}/S_T$. The slope value for this relationship is graphically illustrated in FIG. 14. If the ratio of $S_{BR}$ to $S_T$ is between 1 and 2, then the cathodic neuromodulation may be determined by $1-(½*S_{BR}/S_T)$. The slope value for this relationship is graphically illustrated in FIG. 14. Thus, in the illustrated example, cathodic neuromodulation 1452 is provided when the ratio of $S_{BR}$ to $S_T$ is less than 0.5, anodic neuromodulation 1456 is provided when the ratio of $S_{BR}$ to $S_T$ is more than 2, a first linear relationship 1456 is provided for the "mix" when the cathodic is larger than the anodic, and a second linear relationship 1458 is provided for the mix when the anodic is larger than the cathodic. Other embodiments may implement non-linear relationships between or among the scores.

Figure 15:
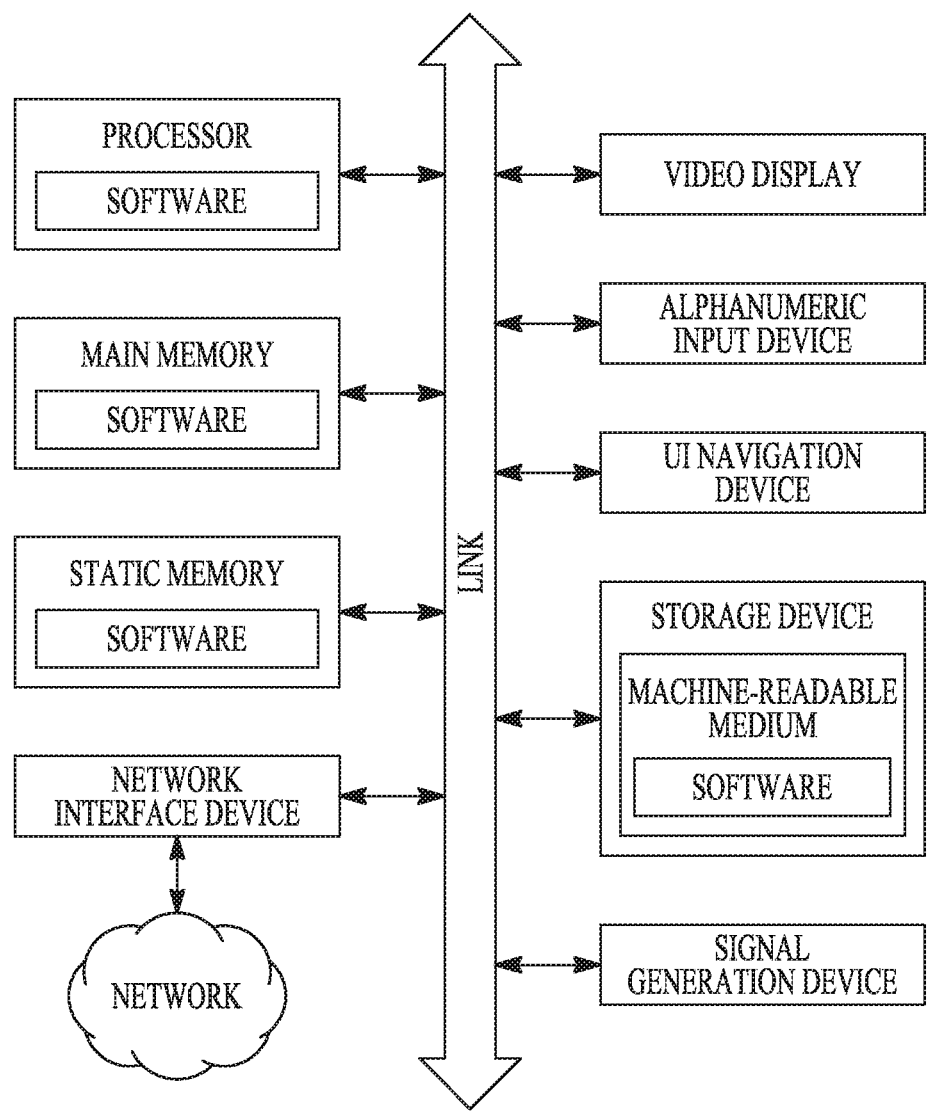
FIG. 15 is a block diagram illustrating a machine in the example form of a computer system, within which a set or sequence of instructions may be executed to cause the machine to perform any one of the methodologies discussed herein.

FIG. 15 is a block diagram illustrating a machine in the example form of a computer system, within which a set or sequence of instructions may be executed to cause the machine to perform any one of the methodologies discussed herein, according to an example embodiment. In alternative embodiments, the machine operates as a standalone device or may be connected (e.g., networked) to other machines. In a networked deployment, the machine may operate in the capacity of either a server or a client machine in server-client network environments, or it may act as a peer machine in peer-to-peer (or distributed) network environments. The machine may be a personal computer (PC), a tablet PC, a hybrid tablet, a personal digital assistant (PDA), a mobile telephone, an implantable pulse generator (IPG), an external remote control (RC), a User's Programmer (CP), or any machine capable of executing instructions (sequential or otherwise) that specify actions to be taken by that machine, Further, while only a single machine is illustrated, the term "machine" shall also be taken to include any collection of machines that individually or jointly execute a set (or multiple sets) of instructions to perform any one or more of the methodologies discussed herein. Similarly, the term "processor-based system" shall be taken to include any set of one or more machines that are controlled by or operated by a processor (e.g., a computer) to individually or jointly execute instructions to perform any one or more of the methodologies discussed herein.

An example of a computer system includes at least one processor (e.g., a central processing unit (CPU), a graphics processing unit (GPU) or both, processor cores, compute nodes, etc.), a main memory and a static memory, which communicate with each other via a link (e.g., bus). The computer system may further include a video display unit, an alphanumeric input device (e.g., a keyboard), and a user interface (UI) navigation device (e.g., a mouse). In one embodiment, the video display unit, input device and UI navigation device are incorporated into a touch screen display. The computer system may additionally include a storage device (e.g., a drive unit), a signal generation device (e.g., a speaker), a network interface device, and one or more sensors (not shown), such as a global positioning system (GPS) sensor, compass, accelerometer, or another sensor. It will be understood that other forms of machines or apparatuses (such as IPG, RC, CP devices, and the like) that are capable of implementing the methodologies discussed in this disclosure may not incorporate or utilize every component depicted in FIG. 15 (such as a GPU, video display unit, keyboard, etc.).

The storage device includes a machine-readable medium on which is stored one or more sets of data structures and instructions (e.g., software) embodying or utilized by any one or more of the methodologies or functions described herein. The instructions may also reside, completely or at least partially, within the main memory, static memory, and/or within the processor during execution thereof by the computer system, with the main memory, static memory, and the processor also constituting machine-readable media.

While the machine-readable medium is illustrated in an example embodiment to be a single medium, the term "machine-readable medium" may include a single medium or multiple media (e.g., a centralized or distributed database, and/or associated caches and servers) that store the one or more instructions. The term "machine-readable medium" shall also be taken to include any tangible (e.g., non-transitory) medium that is capable of storing, encoding or carrying instructions for execution by the machine and that cause the machine to perform any one or more of the methodologies of the present disclosure or that is capable of storing, encoding or carrying data structures utilized by or associated with such instructions. The term "machine-readable medium" shall accordingly be taken to include, but not be limited to, solid-state memories, and optical and magnetic media. Specific examples of machine-readable media include non-volatile memory, including but not limited to, by way of example, semiconductor memory devices (e.g., electrically programmable read-only memory (EPROM), electrically erasable programmable read-only memory (EEPROM)) and flash memory devices; magnetic disks such as internal hard disks and removable disks; magneto-optical disks; and CD-ROM and DVD-ROM disks.

The instructions may further be transmitted or received over a communications network using a transmission medium via the network interface device utilizing any one of a number of well-known transfer protocols (e.g., HTTP). Examples of communication networks include a local area network (LAN), a wide area network (WAN), the Internet, mobile telephone networks, plain old telephone (POTS) networks, and wireless data networks (e.g., Wi-Fi, 3G, and 4G LTE/LTE-A or 5G networks). The term "transmission medium" shall be taken to include any intangible medium that is capable of storing, encoding, or carrying instructions for execution by the machine, and includes digital or analog communications signals or other intangible medium to facilitate communication of such software.

The above detailed description is intended to be illustrative, and not restrictive. The scope of the disclosure should, therefore, be determined with references to the appended claims, along with the full scope of equivalents to which such claims are entitled.

What is claimed is:

1. A method implemented by a system configured for use with multiple available neuromodulation modes for providing a modulation field to modulate a neural target for a neuromodulation therapy, the available neuromodulation modes including an anodic neuromodulation mode for delivering an anodic modulation field to modulate the neural target, a cathodic neuromodulation mode for delivering a cathodic neuromodulation field to modulate the neural target, and a mixed neuromodulation mode for delivering a mixed neuromodulation field to modulate the neural target, wherein the mixed field includes both anodic neuromodulation and cathodic neuromodulation, the neural target having a different tissue reaction to each of the anodic modulation field, the cathodic modulation field and the mixed field, the method comprising:
   entering at least one input into an algorithm configured to identify, based on the at least one input, any one of the anodic neuromodulation mode, the cathodic neuromodulation mode or the mixed neuromodulation mode as a candidate neuromodulation mode for providing the modulation field to modulate the neural target, wherein the at least one input includes at least one of:
   one or more sensor inputs or one or more inputs from smart appliances or one or more user inputs regarding at least one of time of day or mental or physical state; or
   at least one of a user-inputted disease, a user-inputted disease state, a user-inputted symptom-related information, or a user-inputted side effect; and
   implementing the algorithm to identify, based on that at least one input, the candidate neuromodulation mode for providing the modulation field to modulate the neural target for the neuromodulation therapy, the algorithm being configured to output instructions for implementing a system action based on the candidate neuromodulation mode, wherein the system action for the candidate neuromodulation mode includes implementing the candidate neuromodulation mode for delivering the neuromodulation therapy, wherein implementing the candidate neuromodulation mode includes accounting for the different tissue reaction of the neural target to determine a distribution of energy across a plurality of electrodes to provide the modulation field.

2. The method of claim 1, wherein the mixed neuromodulation mode includes a balanced mixed neuromodulation mode that balances a mix of the anodic neuromodulation and the cathodic neuromodulation.

3. The method of claim 1, wherein the implementing the algorithm includes implementing the algorithm to determine a mix of the anodic and cathodic neuromodulation.

4. The method of claim 1, wherein the mixed neuromodulation mode provides a temporal mix with anodic neuromodulation during a time and cathodic neuromodulation during another time.

5. The method of claim 1, wherein the mixed neuromodulation mode provides a spatial mix with a field shape to provide anodic neuromodulation in a first region of the field shape and cathodic neuromodulation in a second region of the field shape.

6. The method of claim 1, wherein the multiple available neuromodulation modes include a neuromodulation mode for delivering neuromodulation that preferentially modulates tissue inclusive of cell bodies and another neuromodulation mode for delivering neuromodulation that preferentially modulates neuron fibers.

7. The method of claim 1, wherein the multiple available neuromodulation modes include neuromodulation modes for delivering different pulse shapes, or different modulation field shapes.

8. The method of claim 1, wherein implementing the algorithm includes implementing the algorithm using an external programming system or a neuromodulator, the external programming system being configured to program the neuromodulator configured to deliver the neuromodulation therapy.

9. The method of claim 1, wherein the entering the input includes entering at least one user-inputted symptom-related information.

10. The method of claim 9, wherein the at least one user-inputted symptom-related information relates to Parkinson's disease.

11. The method of claim 10, wherein the at least one user-inputted symptom-related information includes a score for at least one of bradykinesia, rigidity, or tremor, and the implementing the algorithm to identify one of the neuromodulation modes as the candidate neuromodulation mode is based on the score for the at least one of bradykinesia, rigidity, or tremor.

12. The method of claim 10, wherein the at least one user-inputted symptom-related information includes a score for at least one of freezing of gait, gait, axial symptoms, dementia, and dyskinesias, and the implementing the algorithm to identify one of the neuromodulation modes as the candidate neuromodulation mode is based on the score for the at least one of freezing of gait, gait, axial symptoms, dementia, and dyskinesias.

13. The method of claim 9, wherein the at least one user-inputted symptom-related information further includes medication usage or energy usage for the neuromodulation therapy.

14. The method of claim 9, wherein the user-inputted disease includes a neurodegenerative disease, wherein entering the input further includes entering a stage of the neurodegenerative disease.

15. The method of claim 1, wherein the entering the input includes entering a stage of Parkinson's disease, including at least one of mild, moderate, severe, at least a portion of Unified Parkinson's Disease Rating Scale, Hoehn & Yahr, and medication resistant.

16. The method of claim 1, wherein entering the input includes entering user-inputted side effects.

17. The method of claim 1, wherein the neuromodulation therapy includes deep brain stimulation (DBS).

18. The method of claim 1, wherein the neuromodulation therapy includes spinal cord stimulation (SCS).

19. The method of claim 1, wherein the at least one input includes the at least one sensor input, the system further comprising at least one sensor to provide the at least one sensor input to the algorithm, wherein the at least one sensor includes at least one of:
   a sensor of impedance;
   a sensor of brain activity;
   a sensor of activity in a spinal cord, dorsal horn or dorsal root; or
   a sensor of physical activity or physical state.

20. A non-transitory machine-readable medium including instructions, which when executed by a machine, cause the machine to:
enter at least one input into an algorithm that is configured to identify, based on the at least one input, a candidate neuromodulation mode for providing a modulation field to modulate a neural target for a neuromodulation therapy, including any one of an anodic neuromodulation mode for delivering an anodic modulation field to modulate the neural target, a cathodic neuromodulation mode for delivering a cathodic modulation field to modulate the neural target, or a mixed neuromodulation mode for delivering a mixed neuromodulation field to modulate the neural target, where the mixed field includes both anodic neuromodulation and cathodic neuromodulation, the neural target having a different tissue reaction to each of the anodic modulation field, the cathodic modulation field and the mixed field, wherein the at least one input includes at least one of:
   one or more sensor inputs or one or more user inputs regarding at least one of time of day or mental or physical state; or
   at least one of a user-inputted disease, a user-inputted disease state, a user-inputted symptom-related information, or a user-inputted side effect; and
implement the algorithm to identify, based on the at least one input, the candidate neuromodulation mode for providing the modulation field to modulate the neural target for the neuromodulation therapy, the algorithm being configured to output instructions for implementing an action for the candidate neuromodulation mode, wherein the action for the candidate neuromodulation mode includes implementing the candidate neuromodulation mode for delivering the neuromodulation therapy, and wherein the implementing the candidate neuromodulation mode includes accounting for the different tissue reaction of the neural target to determine a distribution of energy across a plurality of electrodes to provide the modulation field.

* * * * *